United States Patent
O'Neill et al.

(10) Patent No.: US 12,076,378 B2
(45) Date of Patent: *Sep. 3, 2024

(54) USE OF CAR AND BITE TECHNOLOGY COUPLED WITH AN SCFV FROM AN ANTIBODY AGAINST HUMAN THYMIDINE KINASE 1 TO SPECIFICALLY TARGET TUMORS

(71) Applicants: Kim Leslie O'Neill, Provo, UT (US); Scott Weber, Lindon, UT (US)

(72) Inventors: Kim Leslie O'Neill, Provo, UT (US); Scott Weber, Lindon, UT (US)

( * ) Notice: Subject to any disclaimer, the term of this patent is extended or adjusted under 35 U.S.C. 154(b) by 384 days.

This patent is subject to a terminal disclaimer.

(21) Appl. No.: 17/366,708

(22) Filed: Jul. 2, 2021

(65) Prior Publication Data

US 2021/0330770 A1    Oct. 28, 2021

Related U.S. Application Data

(63) Continuation of application No. 16/122,564, filed on Sep. 5, 2018, now Pat. No. 11,052,138, which is a continuation of application No. 15/161,045, filed on May 20, 2016, now Pat. No. 10,434,153.

(60) Provisional application No. 62/204,935, filed on Aug. 13, 2015, provisional application No. 62/164,524, filed on May 20, 2015.

(51) Int. Cl.
| | |
|---|---|
| *A61K 39/00* | (2006.01) |
| *A61P 35/00* | (2006.01) |
| *C07K 14/725* | (2006.01) |
| *C07K 16/28* | (2006.01) |
| *C07K 16/40* | (2006.01) |
| *C07K 16/46* | (2006.01) |

(52) U.S. Cl.
CPC .. *A61K 39/0011* (2013.01); *A61K 39/001162* (2018.08); *A61P 35/00* (2018.01); *C07K 14/7051* (2013.01); *C07K 16/2803* (2013.01); *C07K 16/40* (2013.01); *C07K 16/468* (2013.01); *A61K 2039/505* (2013.01); *A61K 2039/5156* (2013.01); *A61K 2039/5158* (2013.01); *C07K 2317/31* (2013.01); *C07K 2317/34* (2013.01); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 499,629 A | 6/1893 | Ellis |
| 906,682 A | 12/1908 | Birkeland |
| 911,993 A | 2/1909 | Jacobs |
| 916,381 A | 3/1909 | Webster |
| 5,359,046 A | 10/1994 | Capon et al. |
| 7,837,998 B2 | 11/2010 | Lallatin et al. |
| 8,916,381 B1 | 8/2014 | June |
| 8,906,682 B2 | 12/2014 | June et al. |
| 8,911,993 B2 | 12/2014 | June et al. |
| 9,393,268 B2 | 7/2016 | Waldman et al. |
| 9,499,629 B2 | 11/2016 | June |
| 10,415,017 B2 | 9/2019 | ONeill |
| 10,434,153 B1 | 10/2019 | ONeill et al. |
| 10,889,803 B2 | 1/2021 | O'Neill et al. |
| 11,052,138 B2 * | 7/2021 | O'Neill ............ C07K 16/40 |
| 11,352,439 B2 * | 6/2022 | O'Neill ............ C07K 16/2866 |
| 2010/0143290 A1 | 6/2010 | Lallatin |
| 2010/0266495 A1 | 10/2010 | ONeill |
| 2011/0176996 A1 | 7/2011 | ONeill et al. |
| 2014/0242701 A1 | 8/2014 | Shiku et al. |
| 2016/0145348 A1 | 5/2016 | Stephan |
| 2018/0244748 A1 | 1/2018 | Gill et al. |

FOREIGN PATENT DOCUMENTS

| | | |
|---|---|---|
| JP | 2017500869 A | 1/2017 |
| WO | 2010065763 A1 | 6/2010 |
| WO | 2011082345 A2 | 7/2011 |
| WO | 2015063069 A1 | 5/2015 |
| WO | 2015094106 A1 | 6/2015 |
| WO | 2016033331 A1 | 3/2016 |
| WO | 2017019848 A1 | 2/2017 |
| WO | 2017025038 A1 | 2/2017 |
| WO | 2017025944 A2 | 2/2017 |
| WO | 2017049166 A1 | 3/2017 |
| WO | 2017053556 A1 | 3/2017 |
| WO | 2018212770 A1 | 11/2018 |

OTHER PUBLICATIONS

Abken, Hinrich, Driving CARs on the Highway to Solid Cancer: Some Considerations on the Adoptive Therapy with CAR T Cells, Human Gene Therapy, vol. 28, No. 11, 2017, doi:10.1089/hum.2017.115, pp. 1047-1060.

Appendix A of Feb. 29, 2020, Remarks of Mar. 15, 2018 filing in U.S. Appl. No. 15/161,045, by Daniel J. Morath, Ph.D. 8 pages. Long.

Biglari, et al. (2006) "Human monocytes expressing a CEA-specific chimeric CD64 receptor specifically target CEA-expressing tumour cells in vitro and in vivo", Gene Therapy, 13: 602-10.

Bulut, Chlamydia Heat Shock Protein 60 Activates Macrophages and Endothelial Cells Through Toll-Like Receptor 4 and MD2 in a MyD88-Dependent Pathway, 2002, The Journal of Immunology 168:1435-1440, American Association of Immunologists, Inc.

CD Creative Diagnostics, Resources, "4-1BB/4-1BBL Signaling Pathway", https://www.creative-diagnostics.com/4-1bb-4-1bbl-signaling-pathway.htm, accessed Dec. 29, 2020, 2 pgs.

(Continued)

*Primary Examiner* — Robert M Kelly

(57) ABSTRACT

Modified T-cells have paratopes against human TK1 epitopes, are made by producing monoclonal antibodies that are specific to TK1, creating chimeric antigen receptors (CARs) by fusion of the single-chain variable fragments (scFv) of the monoclonal antibodies to T-cell signalling domains, and transducing the CARs to the T-cells.

8 Claims, 11 Drawing Sheets

Specification includes a Sequence Listing.

(56) References Cited

OTHER PUBLICATIONS

Celhar, Teja, et al. "TLR7 And TLR9 Ligands Regulate Antigen Presentation by Macrophages." International Immunology, vol. 28, No. 5, 2016, pp. 223-232.
Darcy et al., Manipulating Immune Cells for Adoptive Immunotherapy of Cancer, Apr. 1, 2014, Current Opinion Immunology, vol. 27: 46-52.
Edwards, Bryan M, et al. "The Remarkable Flexibility of the Human Antibody Repertoire; Isolation of Over One Thousand Different Antibodies to a Single Protein, BLyS." Journal of Molecular Biology, vol. 334, No. 1, 2003, pp. 103-118.
European Patent Office Communication Pursuant to Article 94(3) EPC, Application No. 16801306.8, dated Feb. 14, 2020, 4 pages.
European Patent Office Communication Pursuant to Article 94(3) EPC, Application No. 16801306.8, dated Jan. 30, 2019, 5 pages.
Frohlich, Anne, et al. "Comprehensive Analysis of Tumor Necrosis Factor Receptor TNFRSF9 (4-1BB) DNA Methylation with Regard to Molecular and Clinicopathological Features, Immune Infiltrates, and Response Prediction to Immunotherapy in Melanoma." EBioMedicine, vol. 52, 2020, p. 102647.
Gunaydin, et al. (2014) "Mutations in Toll-Like Receptor 3 Are Associated with Elevated Levels of Rotavirus-Specific IgG Antibodies in IgA-Deficient but Not IgA-Sufficient Individuals", Cancer and Vaccine Immunology, 21(3): 298-301 (Year: 2014).
Kochenderfer, et al. (Apr. 2, 2013) "Treating B-cell cancer with T cells expressing anti-CD19 chimeric antigen receptors", Nature Reviews Clinical Oncology, 10: 267-76.
Langstein, Joachim, et al. "CD137 (ILA/4-1BB), a Member of the TNF Receptor Family, Induces Monocyte Activation via Bidirectional Signaling." The Journal of Immunology (1950), vol. 160, No. 5, 1998, pp. 2488-2494.
Levin, et al. "Evaluation of Macrophage-Specific Promoters Using Lentiviral Delivery in Mice." Gene Therapy, Macmillan Publishers Limited vol. 19, No. 11, 2012, pp. 1041-1047.
Lloyd, et al. "Modelling the Human Immune Response: Performance of a 10 11 Human Antibody Repertoire against a Broad Panel of Therapeutically Relevant Antigens." Protein Engineering, Design Selection, vol. 22, No. 3, 2009, pp. 159-168.
Lo et al., Regression of established renal cell carcinoma in nude mice using lentivirus-transduced human T cells expressing a human anti-CAIX chimeric antigen receptor, Molecular Therapy, Oncolytics, 2014, vol. 1, doi:10.1038/mto.2014.3.
Macrophages on Immunology website (visited Mar. 16, 2018), http://cellular-immunity.blogspot.com/2007/12/macrophages.html 3 pgs.
Murphy et al., The prolonged Life-Span of Alveolar Macrophages, Am J Respir Cell Mol Biol, 2008, pp. 380-385, vol. 38.
Orecchioni, Marco, et al. "Macrophage Polarization: Different Gene Signatures in M1(LPS ) vs. Classically and M2 (LPS-) vs. Alternatively Activated Macrophages." Frontiers in Immunology, vol. 10, 2019, p. 1084.
Palaga et al, Notch signaling is activated by TLR stimulation and regulates macrophage functions, 2008, European Journal of Immunology 38:174-183.
Paul et al., Targeted macrophage cytotoxicity using a nonreplicative live vector expressing a tumor-specific single-chain variable region fragment, Jul. 1, 2000, Human Gene Therapy, Mary Ann Liebert, Inc. Publichers, US, vol. 11, No. 10.
PCT International Search Report and Written Opinion, PCT/IB2016/056140, dated Mar. 17, 2017, 17 pages.
PCT International Search Report and Written Opinion, PCT/US2017/033039, dated Jan. 30, 2018, 10 pages.
Rossi, et al. (Dec. 2, 2013) "A new class of bispecific antibodies to redirect T cells for cancer immunotherapy", MAbs, 6(2): 381-91.
Sarlus, et al. (2017) "Micrglia in Alzheimers disease", The Journal of Clinical Investigation, 127(9): 3240-49. (Year: 2017).
Sharp, et al. (2011) "Abstract 897: Thymidine kinase 1, a novel biomarker specific to the plasma membrane of cancerous cell lines", (Proceedings of the 102nd Annual Meeting of the American Association for Cancer Research, Apr. 2-6, Orlando, FL), Cancer Research, 71(8 Suppl), Abstract 897.
Sinha, Pratima, et al. "Reduction of Myeloid-Derived Suppressor Cells and Induction of M1 Macrophages Facilitate the Rejection of Established Metastatic Disease." Journal of Immunology (Baltimore, Md. : 1950), vol. 174, No. 2, 2005, pp. 636-645.
Wang, Yao-Chun, et al. "Notch Signaling Determines the M1 versus M2 Polarization of Macrophages in Antitumor Immune Responses." Cancer Research, vol. 70, No. 12, 2010, pp. 4840-4849.
Wynn, et al. (2015) "Macrophages in Tissue Repair, Regeneration and Fibrosis", Immunity, 44: 450-462. (Year: 2015).
Yong et al, Using Electroporation to Determine Function of a Chimeric Antigen Receptor in T Cell and Macrophage Cell Lines, The Open Gene Therapey Journal, vol. 5 No. 1, Aug. 23, 2013, pp. 1-11.
Zhang F et al., "A Monoclonal Antibody Specific for Human Thymidine Kinase 1," Jul. 20, 2004, Hybridoma, Liebert, New York, NY, US, vol. 1: 25-34.
Japanese Office Action, Notice of Reasons for Rejection, dated Jan. 31, 2022, Application No. 2020-514655, 8 pgs. wiith translation.
Quatromoni, Jon G., et al., "Tumor-Associated Macrophages: Function, Phenotype, and Link to Prognosis in Human Lung Cancer." Am. Journal Transl. Res., Oct. 2012. 30, vol. 4 (4): pp. 376-389.
Brempelis, et al. (2020) "Genetically engineered macrophages persist in solid tumors and locally deliver therapeutic proteins to activate immune responses." Journal for ImmunoTherapy of Cancer, 8:e001356, 14 pages (Year: 2020).
Japanese Office Action, Decision of Rejection, Mail Date Apr. 22, 2024, Application No. 2022-167762 Thunder Biotech Inc., 6 pgs. With translation.

\* cited by examiner

FIG 7

Sequencing data for the TK1 CAR T cell DNA vector. (Annotated Version)

TK1 CAR T Cell vector nucleotide sequence map (FIG. 7 Cont.)

3' Long Terminal repeat

```
GCAGAATTGCGAACCATGGATTCCACCGTGAACTTTGTCTCCTGGCATGCAAATCGTCAACTTGGCATGCCAAGAATTAATTCG
GATCCAAGCTTAGGCCTGCTCGCTTTCTTGCTGTCCCATTTCTATTAAAGGTTCCTTTGTTCCCTAAGTCCAACTACTAAACTGGG
GGATATTATGAAGGGCCTTGAGCATCTGGATTCTGCCTAGCGCTAAGCTTCCTAACACGAGCCATAGATAGAATAAAAGATTTT
ATTTAGTCTCCAGAAAAAGGGGGGAATGAAAGACCCCACCTGTAGGTTTGGCAAGCTAGCTTAAGTAAGCCATTTTGCAAGGC
ATGGAAAAATACATAACTGAGAATAGAGAAGTTCAGATCAAGGTTAGGAACAGAGAGACAGGCAGAATATGGGCCAAACAGG
ATATCTGTGGTAAGCAGTTCCTGCCCCGGCTCAGGGCCAAGAACAGTTGGAACAGCAGAATATGGGCCAAACAGGATATCTG
TGGTAAGCAGTTCCTGCCCCGGCTCAGGGCCAAGAACAGATGGTCCCCAGATGCGGTCCCGCCCTCAGCAGTTTCTAGAGAAC
CATCAGATGTTTCAGGGGTGCCCCAAGGACCTGAAATGACCCTGTGCCTTATTTGAACTAACCAATCAGTTCGCTTCTCGCTTCT
GTTCGCGCGCTTCTGCTCCCGAGCTCAATAAAAGAGCCCACAACCCCTCACTCGGCGCGCCAGTCCTCCGATAGACTGCGTCG
CCCGGGGTACCCGTATTCCCAATAAAGCCTCTTGCTGTTTGCATCCGAATCGTGGACTCGCTGATCCTTGGGAGGGTCTCCTCA
GATTGATTGACTGCCCACCTCGGGGGGTCTTTCATTCTCGAGAGCTTTGGCGTAATCATGGTCATAGCTGTTTCCTGTGTGAAATT
GTTATCCGCTCACAATTCCACACAACATACGAGCCGGAAGCATAAAGTGTAAAGCCTGGGGTGCCTAATGAGTGAGCTAACTC
ACATTAATTGCGTTGCGCTCACTGCCCGCTTTCCAGTCGGGAAACCTGTCGTGCCAGCTGCATTAATGAATCGGCCAACGCGCG
GGGAGAGGCGGTTTGCGTATTGGGCGCTCTTCCGCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGCGCTTTCTCAATGCTCACGCTG
TAGGTATCTCAGTTCGGTGTAGGTCGTTCGCTCCAAGCTGGGCTGTGTGCACGAACCCCCCGTTCAGCCCGACCGCTGCGCCTT
ATCCGGTAACTATCGTCTTGAGTCCAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTACACTAGAAGGACAGTATTTGGTAT
CTGCGCTCTGCTGAAGCCAGTTACCTTCGGAAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAGATCCTTTGATCTTTTCTACGGGGTCTGACG
CTCAGTGGAACGAAAACTCACGTTAAGGGATTTTGGTCATGAGATTATCAAAAAGGATCTTCACCTAGATCCTTTTAAATTAAA
AATGAAGTTTTAAATCAATCTAAAGTATATATGAGTAAACTTGGTCTGACAGTTACCAATGCTTAATCAGTGAGGCACCTATCT
CAGCGATCTGTCTATTTCGTTCATCCATAGTTGCCTGACTCCCCGTCGTGTAGATAACTACGATACGGGAGGGCTTACCATCTG
GCCCCAGTGCTGCAATGATACCGCGAGACCCACGCTCACCGGCTCCAGATTTATCAGCAATAAACCAGCCAGCCGGAAGGGCC
GAGCGCAGAAGTGGTCCTGCAACTTTATCCGCCTCCATCCAGTCTATTAATTGTTGCCGGGAAGCTAGAGTAAGTAGTTCGCCA
GTTAATAGTTTGCGCAACGTTGTTGCCATTGCTGCTGGCATCGTGGTGTCACGCTCGTCGTTTGGTATGGCTTCATTCAGCTCCG
GTTCCCAACGATCAAGGCGAGTTACATGATCCCCCATGTTGTGCAAAAAAGCGGTTAGCTCCTTCGGTCCTCCGATCGTTGTCA
GAAGTAAGTTGGCCGCAGTGTTATCACTCATGGTTATGGCAGCACTGCATAATTCTCTTACTGTCATGCCATCCGTAAGATGCT
TTTCTGTGACTGGTGAGTACTCAACCAAGTCATTCTGAGAATAGTGTATGCGGCGACCGAGTTGCTCTTGCCCGGCGTCAATAC
GGGATAATACCGCGCCACATAGCAGAACTTTAAAAGTGCTCATCATTGGAAAACGTTCTTCGGGGCGAAAACTCTCAAGGATC
TTACCGCTGTTGAGATCCAGTTCGATGTAACCCACTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGACACGGAAATGTTGAATACTCATACTCTTCCT
TTTTCAATATTATTGAAGCATTTATCAGGGTTATTGTCTCATGAGCGGATACATATTTGAATGTATTTAGAAAAATAAACAAATA
GGGGTTCCGCGCACATTTCCCCGAAAAGTGCCACCTGACGTCTAAGAAACCATTATTATCATGACATTAACCTATAAAAATAGG
CGTATCACGAGGCCCTTTCGTCTTCAAGCTGCCTCGCGCGTTTCGGTGATGACGGTGAAAACCTCTGACACATGCAGCTCCCGG
AGACGGTCACAGCTTGTCTGTAAGCGGATGCCGGGAGCAGACAAGCCCGTCAGGGCGCGTCAGCGGGTGTTGGCGGGTGTC
GGGGCGCAGCCATGACCCAGTCACGTAGCGATAGTTACTATGCGGCATCAGAGCAGATTGTACTGAGAGTGCACCATATGCG
GTGTGAAATACCGCACAGATGCGTAAGGAGAAAATACCGCATCAGGCGCCATTCGCCATTCAGGCTGCGCAACTGTTGGGAA
GGGCGATCGGTGCGGGCCTCTTCGCTATTACGCCAGCTGGCGAAAGGGGGATGTGCTGCAAGGCGATTAAGTTGGGTAACGC
CAGGGTTTTCCCAGTCACGACGTTGTAAAACGACGGCCAGTGAATTAGTACTCTAGCTTAAGTAAGCCATTTTGCAAGGCATG
GAAAAATACATAACTGAGAATAGAGAAGTTCAGA
```

Ampicillin resistance gene aquaporin

Beta lactamase

Fig 7 (cont.)

Sequencing data for the TK1 CAR T cell DNA vector. (FASTA Version)

TK1 CAR T Cell vector nucleotide sequence map

```
TCAAGGTTAG GAACAGAGAG ACAGGAGAAT ATGGGCCAAA CAGGATATCT GTGGTAAGCA      60
GTTCCTGCCC CGGCTCAGGG CCAAGAACAG TTGGAACAGC AGAATATGGG CCAAACAGGA     120
TATCTGTGGT AAGCAGTTCC TGCCCCGGCT CAGGGCCAAG AACAGATGGT CCCCAGATGC     180
GGTCCCGCCC TCAGCAGTTT CTAGAGAACC ATCAGATGTT CCAGGGTGC  CCCAAGGACC     240
TGAAATGACC CTGTGCCTTA TTTGAACTAA CCAATGACTT CGCTTCTCGC TTCTGTCGC      300
GCGCTTCTGC TCCCCGAGCT CAATAAAAGA GCCCACAACC CCTCACTCGG CGCGCCAGTC     360
CTCCGATTGA CTGCGTCGCC CGGGTACCCG TATTCCCAAT AAAGCCTCTT GCTGTTTGCA     420
TCGGGGGTCT TTCATTTGGA GGTTCCACCG AGATTTGGAG ACCCCTGCCC AGGGACCACC     480
GACCCCCCCG CCGGGAGGTA AGCTGGCCAG CGGTCGTTTC GTGTCTGTCT CTGTCTTTGG     540
GCGTGTTTGT GCCGGCATCT AATGTTGCG  CCTGCGTCTG TACTAGTTGG CTAACTAGAT     600
CTGTATCTGG CGGTCCCGCG GAAGAACTGA CGAGTTCGTA TTCCCGGCCG CAGCCCCTGG     660
GAGACGTCCC AGCGGCCTCG GGGGCCCGTT TGTGGCCCA  TTCTGTATCA GTTAACCTAC     720
CCGAGTCGGA CTTTTTGGAG CTCCGCCACT GTCCGAGGGG TACGTGGCTT TGTTGGGGGA     780
CGAGAGACAG AGACACTTCC CGCCCCCGTC TGAATTTTTG CTTTCGGTTT TACGCCGAAA     840
CCGCGCCGCG CGTCTTGTCT GCTGCAGCAT CGTTCTGTGT TGTCTCTGTC TGACTGTGTT     900
TCTGTATTTG TCTGAAAATT AGCTCGACAA AGTTAAGTAA TAGTCCCTCT CTCCAAGCTC     960
ACTTACAGGC GGCCGCATGG ATTTTCAAGT GCAGATTATC AGCTTCCTGC TAATCAGTGC    1020
TTCAGTCATA ATGTCCAGAG GACAAATTGT TCTCTCCCAG TCTCCAGCAA TCCTGTCTGC    1080
ATCTCCAGGG GAGAAGGTCA CAATGACTTG CAGGGCCAGC TCAAGTGTAA GTTACATGCA    1140
CTTTTACCAA CAGAAGCCAG GATCCTCCCC CAAACCCTGG ATTTATGCCA CATCCAACCT    1200
GGCTTCTGGA GTCCCTGCTC GCTTCAGTGG CAGTGGGTCT GGGACCTCTT TCTCTCTCAC    1260
AATCAGCAGA GTGGAGGCTG AAGATGCTGC CACTTATTAC TGCCAGCAGT GGAGTAGTAA    1320
CCCACCCACG TTCGGCTCGG GGACAAAGTT GGAAATAAAA TCAGGTGGAG GAGGGTCTGG    1380
TGGTGGTGGT TCTGGCGGAG GAGGCTCCAT GGCAGTGGTT ACAGGGGTCA ATTCAGAGGT    1440
TCAGCTGCAG CAGTCTGGGG CAGAGCTTGT GAAGCCAGGG GCCTCAGTCA AGTTGTCCTG    1500
CACAGCTTCT GGCTTCAACA TTAAAGACAC CTATATACAC TGGGTGAAGC AGAGGCCTGA    1560
ACAGGGCCTG GAGTGGATTG GAAGGATTGA TCCTGCGAAT GGTAATACTA AATATGACCC    1620
GAAGTTCCAG GGCAAGGCCA CTATAACAAC AGACACATCC TTCAACACAG CCTACCTGCA    1680
GCTCAGCAGC CTGACATCTG AGGACACTGC CGTCTATTAC TGTGCTAAAG TGGGTTACGG    1740
CCACTGGTAC TTCGATGTCT GGGGCGCAGG GACCACGGTC ACCGTCTCCT CAGTCGACAA    1800
GGTGAACAGC ACCACAACTA AACCTGTCCT GAGAACTCCC AGTCCTGTGC ACCCAACTGG    1860
AACCTCACAG CCACAGCGAC CAGAGGATTG CCGACCTCGC GGGAGCGTGA AGGGAACCGG    1920
ACTGGACTTC GCCTGTGATT CTAGTCCAAA ACTCTTTTGG GCACTGGTGG TCGTGGCTGG    1980
CGTGCTCTTT TGCTACGGAC TCCTGGTCAC TGTGGCCCTG TGCGTGATCT GGACCAACTC    2040
CAGGAGAAAT AGACTCCTGC AGGTGACCAC AATGAACATG ACCCCTCGGC GCCAGGACTT   2100
GACACGCAAG CCATACCAGC CTTATGCCCC AGCCAGGGAC TTCGCAGCAT ATAGACCAGC    2160
ACACGCCCGG GCTAAGTTCA GCAGGAGCGC CGAGACAGCT GCAAACCTCC AGGATCCTAA    2220
TCAGCTGTAC AACGAACTCA ATCTGGGGCG AAGGGAGGAA TATGACGTGC TGGAGAAGAA    2280
ACGAGCAAGG GATCCCGAAA TGGGCGGAAA GCAGCAGAGA CGGCGCAACC CTCAGGAGGG    2340
AGTGTACAAT GCTCTGCAGA AGGACAAAAT GGCAGAGGCC TATTCCGAAA TTGGGACCAA    2400
GGGTGAACGA AGGAGAGGGA AAGGTCATGA TGGCCTGTAC CAGGGACTGT CCACCGCTAC    2460
CAAGGATACC TATGACGCAC TCCACATGCA GACCCTCGCC CCAGATGAG  AGAATTCGAG    2520
CATCTTACCG CCATTTATTC CCATATTTGT TCTGTTTTTC TTGATTTGGG TATACATTTA    2580
AATGTTAATA AAACAAAATG GTGGGGCAAT CATTTACATT TTATGGATA  TGTAATTACT    2640
AGTTCAGGTG TATTGCCACA AGACAAACAT GTTAAGAAAC TTTCCCGTTA TTTACGCTCT    2700
GTTCCTGTTA ATCAACCTCT GGATTACAAA ATTTGTGAAA GATTGACTGA TATTCTTAAC    2760
TATGTTGCTC CTTTTACGCT GTGTGGATAT GCTGCTTTAA TGCCTCTGTA TCATGCTATT    2820
GCTTCCCGTA CGGCTTTCGT TTCTCCTCC  TTGTATAAAT CCTGGTTGCT GTCTCTTTAT    2880
GAGGAGTTGT GGCCCGTTGT CCGTCAACGT GGCGTGGTGT GCTCTGTGTT TGCTGACGCA    2940
ACCCCCACTG GCTGGGGCAT TGCCACCACC TGTCAACTCC TTTCTGGGAC TTTCGCTTTC    3000
CCCCTCCCGA TCGCCACGGC AGAACTCATC GCCGCCTGCC TTGCCCGCTG CTGGACAGGG    3060
GCTAGGTTGC TGGGCACTGA TAATTCCGTG GTGTTGTCGG GAAGCTGAC  GTCCTTTCCA    3120
TGGCTGCTCG CCTGTGTTGC CAACTGGATC CTGCGCGGGA CGTCCTTCTG CTACGTCCCT    3180
TCGGCTCTCA ATCCAGCGGA CCTCCCTTCC GAGGCCTTC  TGCCGGTTCT GCGGCCTCTC    3240
CCGCGTCTTC GCTTTCGGCC TCCGACGAGT CGGATCTCCC TTTGGGCCGC CTCCCCGCCT    3300
```

(FIG. 7 cont.)

```
GTTCGCCTC GGCGTCCGGT CCGTGTTGCT TGGTCGTCAC CTGTGCAGAA TTGCGAACCA 3360
TGGATTCCAC CGTGAACTTT GTCTCCTGGC ATGCAAATCG TCAACTTGGC ATGCCAAGAA 3420
TTAATTCGGA TCCAAGCTTA GGCCTGCTCG CTTTCTTGCT GTCCCATTTC TATTAAAGGT 3480
TCCTTTGTTC CCTAAGTCCA ACTACTAAAC TGGGGGATAT TATGAAGGGC CTTGAGCATC 3540
TGGATTCTGC CTAGCGCTAA GCTTCCTAAC ACGAGCCATA GATAGAATAA AAGATTTTAT 3600
TTAGTCTCCA GAAAAAGGGG GGAATGAAAG ACCCCACCTG TAGGTTTGGC AAGCTAGCTT 3660
AAGTAAGCCA TTTTGCAAGG CATGGAAAAA TACATAACTG AGAATAGAGA AGTTCAGATC 3720
AAGGTTAGGA ACAGAGAGAC AGGAGAATAT GGGCCAAACA GGATATCTGT GGTAAGCAGT 3780
TCCTGCCCCG GCTCAGGGCC AAGAACAGTT GGAACAGCAG AATATGGGCC AAACAGGATA 3840
TCTGTGGTAA GCAGTTCCTG CCCCGGCTCA GGGCCAAGAA CAGATGGTCC CCAGATGCGG 3900
TCCCGCCCTC AGCAGTTCCT AGAGAACCAT CAGATGTTTC CAGGGTGCCC CAAGGACCTG 3960
AAATGACCCT GTGCCTTATT TGAACTAACC AATCAGTTCG CTTCTCGCTT CTGTTCGCGC 4020
GCTTCTGCTC CCGAGCTCA ATAAAGAGC CCACAACCCC TCACTCGGCG CGCCAGTCCT 4080
CCGATAGACT GCGTCGCCCG GGTACCCGT ATTCCCAATA AAGCCTCTTG CTGTTTGCAT 4140
CCGAATCGTG GACTCGCTGA TCTTGGGAG GTCTCCTCA GATTGATTGA CTGCCCACCT 4200
CGGGGGTCTT TCATTCTGA GAGCTTGGC GTAATCATGG TCATAGCTGT TTCCTGTGTG 4260
AAATTGTTAT CCGCTCACAA TTCCACACAA CATACGAGCC GGAAGCATAA AGTGTAAAGC 4320
CTGGGGTGCC TAATGAGTGA GCTAACTCAC ATTAATTGCG TTGCGCTCAC TGCCCGCTTT 4380
CCAGTCGGGA AACCTGTCGT GCCAGCTGCA TTAATGAATC GGCCAACGCG CGGGGAGAGG 4440
CGGTTTGCGT ATTGGGCGCT CTTCCGCTTC CTCGCTCACT GACTCGCTGC GCTCGGTCGT 4500
TCGGCTGCGG CGAGCGGTAT CAGCTCACTC AAAGGCGGTA ATACGGTTAT CCACAGAATC 4560
AGGGGATAAC GCAGGAAAGA ACATGTGAGC AAAAGGCCAG CAAAAGGCCA GGAACCGTAA 4620
AAAGGCCGCG TTGCTGGCGT TTTTCCATAG GCTCCGCCCC CCTGACGAGC ATCACAAAAA 4680
TCGACGCTCA AGTCAGAGGT GGCGAAACCC GACAGGACTA TAAAGATACC AGGCGTTTCC 4740
CCCTGGAAGC TCCCTCGTGC GCTCTCCTGT TCCGACCCTG CCGCTTACCG GATACCTGTC 4800
CGCCTTTCTC CCTTCGGGAA GCGTGGCGCT TTCTCAATGC TCACGCTGTA GGTATCTCAG 4860
TTCGGTGTAG GTCGTTCGCT CCAAGCTGGG CTGTGTGCAC GAACCCCCCG TTCAGCCCGA 4920
CCGCTGCGCC TTATCCGGTA ACTATCGTCT TGAGTCCAAC CCGGTAAGAC ACGACTTATC 4980
GCCACTGGCA GCAGCCACTG GTAACAGGAT TAGCAGAGCG AGGTATGTAG GCGGTGCTAC 5040
AGAGTTCTTG AAGTGGTGGC CTAACTACGG CTACACTAGA AGGACAGTAT TTGGTATCTG 5100
CGCTCTGCTG AAGCCAGTTA CCTTCGGAAA AAGAGTTGGT AGCTCTTGAT CCGGCAAACA 5160
AACCACCGCT GGTAGCGGTG GTTTTTTTGT TTGCAAGCAG CAGATTACGC GCAGAAAAAA 5220
AGGATCTCAA GAAGATCCTT TGATCTTTTC TACGGGGTCT GACGCTCAGT GGAACGAAAA 5280
CTCACGTTAA GGGATTTTGG TCATGAGATT ATCAAAAAGG ATCTTCACCT AGATCCTTTT 5340
AAATTAAAAA TGAAGTTTTA AATCAATCTA AGTATATAT GAGTAAACTT GGTCTGACAG 5400
TTACCAATGC TTAATCAGTG AGGCACCTAT CTCAGCGATC TGTCTATTTC GTTCATCCAT 5460
AGTGCCTGA CTCCCCGTCG TGTAGATAAC TACGATACGG GAGGGCTTAC CATCTGGCCC 5520
CAGTGCTGCA ATGATACCGC GAGACCCACG CTCACCGGCT CCAGATTTAT CAGCAATAAA 5580
CCAGCCAGCC GGAAGGGCCG AGCGCAGAAG TGGTCCTGCA ACTTTATCCG CCTCCATCCA 5640
GTCTATTAAT TGTTGCCGGG AAGCTAGAGT AAGTAGTTCG CCAGTTAATA GTTTGCGCAA 5700
CGTTGTTGCC ATTGCTGCTG GCATCGTGGT GTCACGCTCG TCGTTTGGTA TGGCTTCATT 5760
CAGCTCCGGT TCCCAACGAT CAAGGCGAGT TACATGATCC CCATGTTGT GCAAAAAAGC 5820
GGTTAGCTCC TTCGGTCCTC CGATCGTTGT CAGAAGTAAG TTGGCCGCAG TGTTATCACT 5880
CATGGTTATG GCAGCACTGC ATAATTCTCT TACTGTCATG CCATCCGTAA GATGCTTTTC 5940
TGTGACTGGT GAGTACTCAA CCAAGTCATT CTGAGAATAG TGTATGCGGC GACCGAGTTG 6000
CTCTTGCCCG GCGTCAATAC GGGATAATAC CGCGCCACAT AGCAGAACTT TAAAAGTGCT 6060
CATCATTGGA AAACGTTCTT CGGGGCGAAA ACTCTCAAGG ATCTTACCGC TGTTGAGATC 6120
CAGTTCGATG TAACCCACTC GTGCACCCAA CTGATCTTCA GCATCTTTTA CTTTCACCAG 6180
CGTTTCTGGG TGAGCAAAAA CAGGAAGGCA AAATGCCGCA AAAAAGGGAA TAAGGGCGAC 6240
ACGGAAATGT TGAATACTCA TACTCTTCCT TTTTCAATAT TATTGAAGCA TTTATCAGGG 6300
TTATTGTCTC ATGAGCGGAT ACATATTTGA ATGTATTTAG AAAAATAAAC AAATAGGGGT 6360
TCCGCGCACA TTTCCCCGAA AAGTGCCACC TGACGTCTAA GAAACCATTA TTATCATGAC 6420
ATTAACCTAT AAAAATAGGC GTATCACGAG GCCCTTTCGT CTTCAAGCTG CCTCGCGCGT 6480
TTCGGTGATG ACGGTGAAAA CCTCTGACAC ATGCAGCTCC CGGAGACGGT CACAGCTTGT 6540
CTGTAAGCGG ATGCCGGGAG CAGACAAGCC CGTCAGGGCG CGTCAGCGGG TGTTGGCGGG 6600
TGTCGGGGCG CAGCCATGAC CCAGTCACGT AGCGATAGTT ACTATGCGGG ATCAGAGCAG 6660
ATTGTACTGA GAGTGCACCA TATGCGGTGT GAAATACCGC ACAGATGCGT AAGGAGAAAA 6720
TACCGCATCA GGCGCCATTC GCCATTCAGG CTGCGCAACT GTTGGGAAGG GCGATCGGTG 6780
CGGGCCTCTT CGCTATTACG CCAGCTGGCG AAAGGGGGAT GTGCTGCAAG GCGATTAAGT 6840
TGGGTAACGC CAGGGTTTTC CCAGTCACGA CGTTGTAAAA CGACGGCCAG TGAATTAGTA 6900
CTCTAGCTTA AGTAAGCCAT TTTGCAAGGC ATGGAAAAAT ACATAACTGA GAATAGAGAA 6960
GTTCAGA 6967
```

FIG. 8

TK1 Car T cell protein sequence

Signal peptide

MDFQVQIISFLLLSASVI

CB1 light chain

MSRGQIVLSQSPAILSASPGEKVTMTCRASSSVSYMHFYQQKPGSSPKPWIYATSNLASGVPARFSGSGSGTSFSLTISR
VEAEDAATYYCQQWSSNPPTFGSGTKLEIK

Glycine-serine linker

SGGGGSGGGGSGGGGS

CB1 heavy chain

MAVVTGVNSEVQLQQSGAELVKPGASVKLSCTASGFNIKDTYIHWVKQRPEQGLEWIGRIDPANGNTKYDPKFQGKA
TITTDTSFNTAYLQLSSLTSEDTAVYYCAKVGYGHWYFDVWGAGTTVTVSSVD

SalI

VD

CD8α hinge

KVNSTTTKPVLRTPSPVHPTGTSQPQRPEDCRPRGSVKGTGLDFACD

CD28

SSPKLFWALVVVAGVLFCYGLLVTVALCVIWTNSRRNRLLQVTTMNMTPRRPGLTRKPYQPYAPARDFAAYRPAHA

CD3 zeta

RAKFSRSAETAANLQDPNQLYNELNLGRREEYDVLEKKRARDPEMGGKQQRRRNPQEGVYNALQKDKMAEAYSEIGT
KGERRRGKGHDGLYQGLSTATKDTYDALHMQTLAPR

FIG. 9

TK1 CAR T cell Nucleotide and protein sequence alignment 1533 nucleotides, 511 amino acids.

```
   1 ATGGATTTTCAAGTG CAGATTATCAGCTTC CTGCTAATCAGTGCT TCAGTCATAATGTCC AGAGGACAAATTGTT
   1 M  D  F  Q  V   Q  I  I  S  F    L  L  I  S  A    S  V  I  M  S    R  G  Q  I  V
  76 CTCTCCAGTCTCCA GCAATCCTGTCTGCA TCTCCAGGGGAGAAG GTCACAATGACTTGC AGGGCCAGCTCAAGT
  26 L  S  Q  S  P   A  I  L  S  A    S  P  G  E  K    V  T  M  T  C    R  A  S  S  S
 151 GTAAGTTACATGCAC TTTTACCAACAGAAG CCAGGATCCTCCCCC AAACCCTGGATTTAT GCCACATCCAACCTG
  51 V  S  Y  M  H   F  Y  Q  Q  K    P  G  S  S  P    K  P  W  I  Y    A  T  S  N  L
 226 GCTTCTGGAGTCCCT GCTCGCTTCAGTGGC AGTGGGTCTGGGACC TCTTTCTCTCTCACA ATCAGCAGAGTGGAG
  76 A  S  G  V  P   A  R  F  S  G    S  G  S  G  T    S  F  S  L  T    I  S  R  V  E
 301 GCTGAAGATGCTGCC ACTTATTACTGCCAG CAGTGGAGTAGTAAC CCACCCACGTTCGGC TCGGGGACAAAGTTG
 101 A  E  D  A  A   T  Y  Y  C  Q    Q  W  S  S  N    P  P  T  F  G    S  G  T  K  L
 376 GAAATAAAATCAGGT GGAGGAGGGTCTGGT GGTGGTGGTTCTGGC GGAGGAGGCTCCATG GCAGTGGTTACAGGG
 126 E  I  K  S  G   G  G  G  S  G    G  G  G  S  G    G  G  G  S  M    A  V  V  T  G
 451 GTCAATTCAGAGGTT CAGCTGCAGCAGTCT GGGGCAGAGCTTGTG AAGCCAGGGGCCTCA GTCAAGTTGTCCTGC
 151 V  N  S  E  V   Q  L  Q  Q  S    G  A  E  L  V    K  P  G  A  S    V  K  L  S  C
 526 ACAGCTTCTGGCTTC AACATTAAAGACACC TATATACACTGGGTG AAGCAGAGGCCTGAA CAGGGCCTGGAGTGG
 176 T  A  S  G  F   N  I  K  D  T    Y  I  H  W  V    K  Q  R  P  E    Q  G  L  E  W
 601 ATTGGAAGGATTGAT CCTGCGAATGGTAAT ACTAAATATGACCCG AAGTTCCAGGGCAAG GCCACTATAACAACA
 201 I  G  R  I  D   P  A  N  G  N    T  K  Y  D  P    K  F  Q  G  K    A  T  I  T  T
 676 GACACATCCTTCAAC ACAGCCTACCTGCAG CTCAGCAGCCTGACA TCTGAGGACACTGCC GTCTATTACTGTGCT
 226 D  T  S  F  N   T  A  Y  L  Q    L  S  S  L  T    S  E  D  T  A    V  Y  Y  C  A
 751 AAAGTGGGTTACGGC CACTGGTACTTCGAT GTCTGGGGCGCAGGG ACCACGGTCACCGTC TCCTCAGTCGACAAG
 251 K  V  G  Y  G   H  W  Y  F  D    V  W  G  A  G    T  T  V  T  V    S  S  V  D  K
 826 GTGAACAGCACCACA ACTAAACCTGTCCTG AGAACTCCCAGTCCT GTGCACCCAACTGGA ACCTCACAGCCACAG
 276 V  N  S  T  T   T  K  P  V  L    R  T  P  S  P    V  H  P  T  G    T  S  Q  P  Q
 901 CGACCAGAGGATTGC CGACCTCGCGGGAGC GTGAAGGGAACCGGA CTGGACTTCGCCTGT GATTCTAGTCCAAAA
 301 R  P  E  D  C   R  P  R  G  S    V  K  G  T  G    L  D  F  A  C    D  S  S  P  K
 976 CTCTTTTGGGCACTG GTGGTCGTGGCTGGC GTGCTCTTTTGCTAC GGACTCCTGGTCACT GTGCCCTGTGCGTG
 326 L  F  W  A  L   V  V  V  A  G    V  L  F  C  Y    G  L  L  V  T    V  A  L  C  V
1051 ATCTGGACCAACTCC AGGAGAAATAGACTC CTGCAGGTGACCACA ATGAACATGACCCCT CGGCGCCCAGGACTG
 351 I  W  T  N  S   R  R  N  R  L    L  Q  V  T  T    M  N  M  T  P    R  R  P  G  L
1126 ACACGCAAGCCATAC CAGCCTTATGCCCCA GCCAGGACTTCGCA GCATATAGACCAGCA CACGCCCGGGCTAAG
 376 T  R  K  P  Y   Q  P  Y  A  P    A  R  D  F  A    A  Y  R  P  A    H  A  R  A  K
1201 TTCAGCAGGAGCGCC GAGACAGCTGCAAAC CTCCAGGATCCTAAT CAGCTGTACAACGAA CTCAATCTGGGGCGA
 401 F  S  R  S  A   E  T  A  A  N    L  Q  D  P  N    Q  L  Y  N  E    L  N  L  G  R
1276 AGGGAGGAATATGAC GTGCTGGAGAAGAAA CGAGCAAGGGATCCC GAAATGGGCGGAAAG CAGCAGAGACGGCGC
 426 R  E  E  Y  D   V  L  E  K  K    R  A  R  D  P    E  M  G  G  K    Q  Q  R  R  R
1351 AACCCTCAGGAGGGA GTGTACAATGCTCTG CAGAAGGACAAAATG GCAGAGGCCTATTCC GAAATTGGGACCAAG
 451 N  P  Q  E  G   V  Y  N  A  L    Q  K  D  K  M    A  E  A  Y  S    E  I  G  T  K
1426 GGTGAACGAAGGAGA GGGAAAGGTCATGAT GGCCTGTACCAGGGA CTGTCCACCGCTACC AAGGATACCTATGAC
 476 G  E  R  R  R   G  K  G  H  D    G  L  Y  Q  G    L  S  T  A  T    K  D  T  Y  D
1501 GCACTCCACATGCAG ACCCTCGCCCCAGA TGA
 501 A  L  H  M  Q   T  L  A  P  R    *
```

USE OF CAR AND BITE TECHNOLOGY COUPLED WITH AN SCFV FROM AN ANTIBODY AGAINST HUMAN THYMIDINE KINASE 1 TO SPECIFICALLY TARGET TUMORS

CROSS REFERENCE TO RELATED APPLICATIONS

Priority is claimed from U.S. patent application Ser. No. 16/122,564, filed Sep. 5, 2018, pending, which claims priority to U.S. patent application Ser. No. 15/161,045, filed May 20, 2016, now U.S. Pat. No. 10,434,153, issued on Oct. 8, 2019, which itself claims priority from U.S. Provisional Patent Application 62/164,524, filed May 20, 2015, and from U.S. Provisional Patent Application 62/204,935, filed Aug. 14, 2015, which are hereby incorporated by reference.

BACKGROUND

Although efforts in cancer research have been ongoing for more than 20 years, cancer still accounts for more deaths than heart disease in persons younger than 85 years. Very little progress has been made in the past 30 years to decrease cancer mortality rates and incidence rates. In 2014, there will be an estimated 1,665,540 new cancer cases diagnosed and 585,720 cancer deaths in the US. Cancer remains the second most common cause of death in the US, accounting for nearly 1 of every 4 deaths. [1] It is accepted that while there has been some isolated progress with respect to a few types of cancers (breast, prostate, colon), overall, cancer researchers in the past 30 years have made very little headway against this devastating disease.

Although there has been very little progress, many novel chemotherapies that employ the use of specific antibodies are now showing promise in clinical trials. These new immunotherapies include the use of antibodies and immune cell therapies, coupled with cytokine administration, that are targeting specific tumor types and allowing significant progress in several cancer fields. Many of these chemotherapies target very specific subtypes of cancer, such as treatments with Herceptin (an antibody therapy) used in approximately 10% of breast cancers.

Antibodies against tumor associated epitopes, are proving useful in many tumor therapies but are limited to antigens presented on the cell surface of tumors. Several antibodies have been identified and exploited against multiple types of cancers using passive immunization. Notable examples include rituximab (anti-CD20 for B-cell lymphomas) and trastuzumab (anti-HER-2/neu for certain breast cancers). [6] Therapeutic antibodies have had success against tumors, eliciting both complement-mediated responses and antibody-dependent cellular cytotoxicity (ADCC). However, administration of an anti-cancer antibody as a monotherapy is rare, and these are often combined with more traditional chemotherapy. [4]

However, unless researchers are able to identify a cancer specific yet universal therapy to target all cancers, progress in the fight against cancer will also be limited. In the present study, we introduce the potential for one such novel immunotherapy: Thymidine Kinase 1 (TK1), a tumor biomarker known to be unregulated as an early event in virtually all types of major cancers.

Thymidine Kinase 1 (TK1) is a well-known nucleotide salvage pathway enzyme that has largely been studied in the context of its overexpression in tumors. Since TK was initially popularized by its expression in the serum of cancer patients (sTK), its diagnostic and prognostic potential has been studied extensively. For example, several studies have demonstrated that sTK1 in many different cancer patients is elevated in a stage-like manner with a higher level of TK1 indicating a more advanced tumor. [12]

Other studies have investigated the prognostic potential of TK1. One such study demonstrates that the TK1 levels in primary breast tumors can be used to predict recurrence. Other exciting TK1 prognostic studies show significant reductions in sTK1 levels when patients respond to treatment while sTK1 levels continue to rise in patients who do not appear to respond to their treatment. It is also known that prior to recurrence, sTK1 levels begin to rise and in one study it was noted that in some cases, by measuring sTK1 levels recurrence could be predicted "1-6 months before the onset of clinical symptoms." Several other studies confirm the rich potential of TK1 as a diagnostic and prognostic indicator of cancer [13].

Although the diagnostic and prognostic potential of TK1 has been well established, the therapeutic potential of TK1 remains veiled in comparison. While it is true that HSV-TK has been used in gene therapy and PET imaging utilizes TK to identify proliferating cancer cells, few, if any studies address the possibility of a TK1 immunotherapy. Perhaps this is primarily because TK1 is a known cytosolic protein. We have recently discovered that TK1 is expressed not only in cancer cells but also on the surface membrane of all cancer types and is therefore a very viable target for tumor immunotherapy.

T cells are capable of inducing potent anti-tumor responses, however, T cells that would most efficiently respond to peptide-MHC epitopes on the surface of tumors are often subjected to clonal tolerance or deletion, as many of these epitopes are very similar or identical to self-epitopes. T-cell therapies have involved genetic modification of T cells in vitro by introduction of TCRs against tumor-associated T-cell epitopes. This strategy has shown promise, but various challenges surrounding T-cell epitopes in general, as well as potential mispairing of introduced TCR with endogenous TCR, remain [3]. To harness the power of T cells in the fight against tumors, several methods have been designed that allow T cells to respond to traditional antibody epitopes.

Chimeric antigen receptors (CARs), consisting of extracellular antibody fragments directed against a tumor epitope fused to intracellular T-cell signaling domains, have been transduced into T cells, endowing them with a novel specificity toward a non-MHC restricted epitope [3]. Chimeric antigen receptors (CARs) are recombinant receptors that provide both surface antigen-binding and T-cell-activating functions. A number of CARs has been reported over the past decade, targeting an array of cell surface tumor antigens. Their biologic functions have dramatically changed following the introduction of tripartite receptors comprising a costimulatory domain, termed second-generation CARs. These have recently shown clinical benefit in patients treated with CD19-targeted autologous T cells. CARs may be combined with costimulatory ligands, chimeric costimulatory receptors, or cytokines to further enhance T-cell potency, specificity, and safety. CARs represent a new class of drugs with exciting potential for cancer immunotherapy. [3]

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell; with transfer of their coding sequence facilitated by retroviral vectors.

Upon their expression in T lymphocytes, CARs direct potent, targeted immune responses that have recently shown encouraging clinical outcomes in a subset of patients with B-cell malignancies. This application brings together this new technology with our discovery that TK1 is expressed on the surface of cancer cells, by using a specifically built CAR that has an scFv from our anti human TK1 antibody to utilize the potential of CARs and the TK1 technology to attack tumor cells in vivo. Our recent discovery that TK1 is found on the surface of cancer cells and not normal cells allows the targeted application of CAR technology specific targeting TK1 surface expressing tumors.

The most common CAR formats currently being evaluated include a scFv targeting domain linked to a spacer, trans membrane domain, and intracellular domains from the T-cell receptor CD3s subunit and co-stimulatory domains, such as CD28, OX40 or 4-1BB.21 CAR-based strategies continue to be pursued against a number of tumor-associated epitopes. [4]. Results from recent clinical trials demonstrate the effectiveness of CAR-transduced T cells targeted against the B cell epitope CD19 in achieving long-term remission from refractory chronic lymphocytic leukemia (CLL) when transferred as a monotherapy following lymphodepleting chemotherapy [5].

Referring to FIG. 1 is shown a TK1 specific CART cell that recognizes TK1 as a target on cancer cells. In the ligand binding domain ectodomain is shown a signal peptide and an antigen recognition domain is usually an scFv. A spacer region links the antigen binding domain to the transmembrane domain.

The transmembrane domain is a hydrophobic alpha helix that spans the membrane. Generally, the transmembrane domain from the most membrane proximal component of the endodomain is used.

After antigen recognition receptors cluster in the endodomain and a signal is transmitted to the cell. In an aspect of CARs, there is the intracellular domain from the CD3-zeta (CD3 ζ)-chain, which is the primary transmitter of signals from endogenous T-cell receptors (TCRs). There may be added intracellular signaling domains from various costimulatory protein receptors, such as CD3-zeta and additional co-stimulatory signaling. ZAP-70 also is part of the T cell receptor, and plays a critical role in T-cell signaling.

Another strategy to target T cells to precise antibody epitopes takes advantage of a long-studied type of molecule called "bispecific antibody," which links an anti-cancer antibody with an antibody recognizing CD3 subunits.

These have recently been termed BiTEs (bispecific T-cell engagers). A single-chain variable fragment (scFv) that binds a tumor epitope is linked to a second scFv that binds an invariant portion of the T-cell receptor complex, resulting in activation and targeting of effector T cells against the tumor epitope, regardless of the TCR-mediated specificity of the T cells. Evidence shows that these reagents are considerably more potent than antibodies against tumor cells alone. BiTEs have been constructed targeting more than ten tumor associated epitopes, including blinatumomab against CD19 (for B cell leukemias), and MT-110 against EpCAM (for various adenocarcinomas and cancer stem cells), both being currently evaluated in clinical trials. High response rates for relapse-free survival and elimination of minimal residual disease were found in refractory acute lymphoblastic leukemia (ALL) patients receiving blinatumomab in clinical trials [6].

Referring to FIG. 2, BiTEs are fusion proteins consisting of two single-chain variable fragments (scFvs) of different antibodies, or amino acid sequences from four different genes, on a single peptide chain. One of the scFvs binds to T cells via the CD3 receptor, and the other to a tumor cell via a tumor specific molecule, Like other bispecific antibodies, and unlike ordinary monoclonal antibodies, BiTEs form a link between T cells and tumor cells. This causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells.

While both of these strategies have shown promising results, it is not yet clear under what conditions the CAR approach vs. the BiTE approach might be preferred. The optimal utilization of this knowledge would be in the production of a chimeric antigen receptor (CAR), or BiTEs utilizing the power of a monoclonal antibody produced against human TK1 coupled with the ability of T cells to destroy tumor cells. This is the basis of this application. Use your figure which is too general and make it more specific FIG. 3 represents how engineered T-cells (by CARs ( ) can be used therapeutically by engineering cells from the patient's own body and infusing the T-cell back into the patient.

In BiTEs two single chain variable fragments are bound by a linker, one ScFv binds a tumor antigen and the other binds a tumor antigen, activating T cells and bringer closer them to the tumor cell, the antibody binds CD3 activating the T cell and the other just bind the tumor cell.

SUMMARY

An aspect is technology that would allow the use of a CAR or BiTE produced with a scFv from a humanized or non-human mammal (such as mouse) monoclonal antibody to TK1, that could be used with appropriate genetic engineering to manipulate lymphocytes (possibly T cells but may include other immune cells) ultimately from a patient but not limited to such, to treat a disease such as cancer. That fact that TK1 is on the surface of cancer cells and not on the surface of any normal cell is a major part of the discovery, as this knowledge can be used to allow the T cells to be directed specifically to the tumor cells.

Another aspect lies in the fact that using our specifically generated antibodies to human TK1 we have discovered that TK1 is expressed on the surface of human cancer cells and not on the surface of normal cells and thereby can be used to target CARs and BiTEs to the tumors.

As aspect is CARs and BiTEs using the monoclonal antibodies, such as BYU 74 BYU 72 and CB 001 that we have developed that bind specifically to TK1 on the surface of cancer cells. Antibodies specific to human TK1 are disclosed in U.S. patent application Ser. No. 12/982,250, and U.S. Pat. Nos. 7,837,998, 7,311,906, and 5,698,409, which are hereby incorporated by reference, and F. Zhang, X. Shao, J. G. Robison, B. K. Murray, and K. L. O'Neill. Hybridoma. February 2001, 20(1): 25-34. doi:10.1089/027245701300060382.

The CARs technology and BiTEs technology used disclosed herein can be used to modify macrophages as well as T cells. This may be combined with macrophage tissue-specific promoters directed toward the cancer tissue to eliminate targeting of TK1 is the blood serum and direct to TK1 on cell surfaces.

Sequencing data for the TK1 CAR T cell DNA vector (SEQ ID NO: 1).

Figure 5:
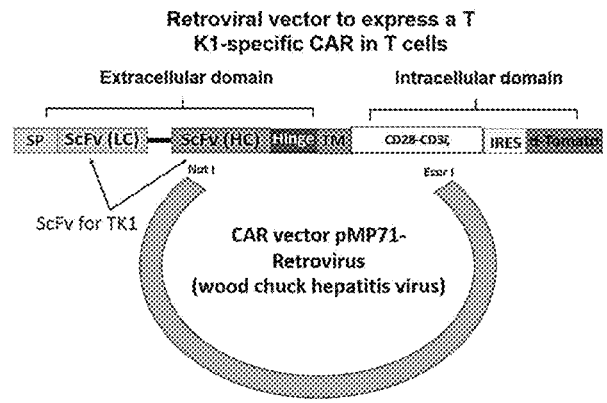
FIG. 5 is a construct of the TK1 CART cell vector. Retroviral mediated gene transfer. 293GPG human retroviral packaging cells are transfected with the vector of interest, which is packaged transiently in vesicular stomatitis virus (VSV) G pseudotyped particles. These particles are used to deliver the vector to PG13 cells, which achieve stable packaging of GALV pseudotyped particles that are suitable for infection of human T-cells.

FIG. 8 shows the sequence of the TK1 T cell CAR protein as FIG. 5. Therein depicted are the amino acid sequence of the signal peptide (SEQ ID NO:2): the CB1 light chain (SEQ ID NO:3): the glycine-serine linker (SEQ ID NO:4) the CB1 heavy chain (SEQ ID NO:5): the CD8α hinge (SEQ ID NO:6); the CD28 costimulatory domain (SEQ ID NO:7): and the CD3 zeta costimulatory domain (SEQ ID NO:8).

FIG. 9 TK1 CAR T cell Nucleotide (SEQ ID NO:1) and protein sequence (SEQ ID NOs:2-8 linked in order) alignment.

DETAILED DESCRIPTION

Example

This is a specific example of how CAR transduced T-cells can be made.

Figure 1:
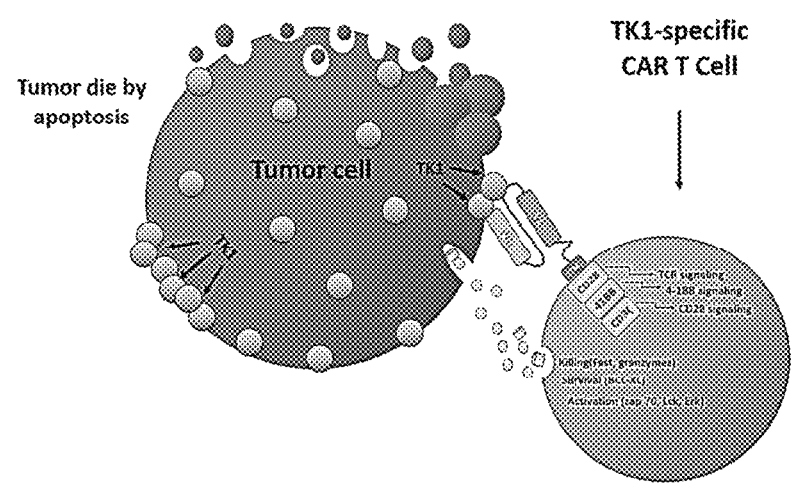
FIG. 1 A TK1 specific CART Cell recognizes a cancer cell using TK1 on the surface as a target. CAR T cells become activated upon recognition of the cancer cell inducing cell death by apoptosis and lysis.
Figure 2:
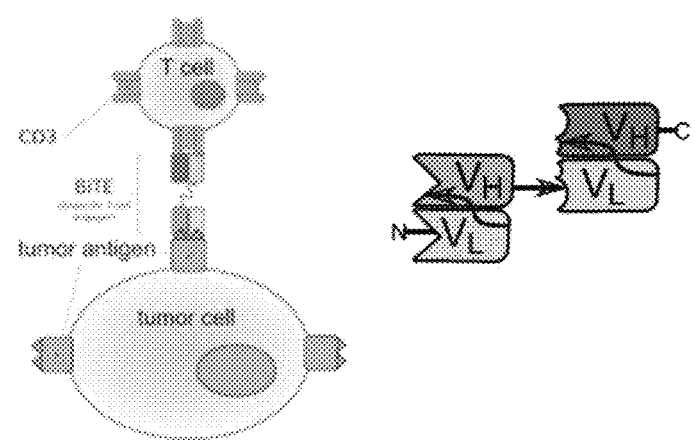
FIG. 2 depicts a generalized prior-art BITEs.
Figure 3:
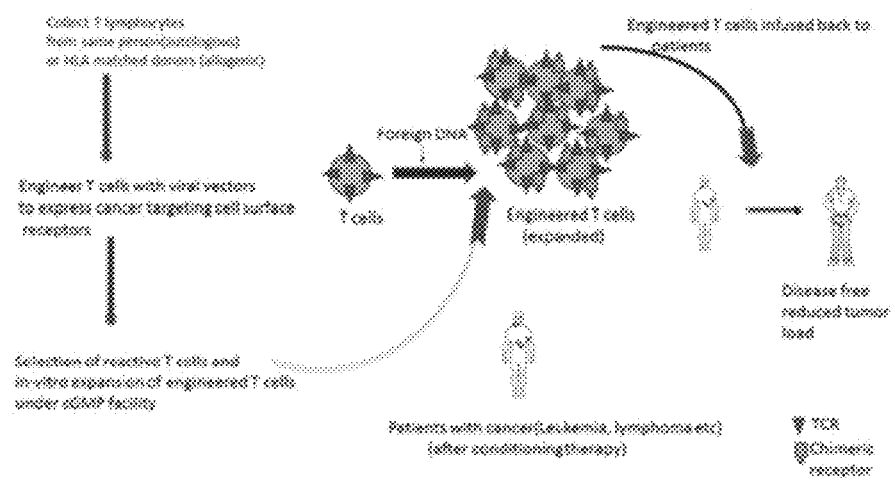
FIG. 3 depicts a therapeutic method using engineered T cells.
Figure 4:
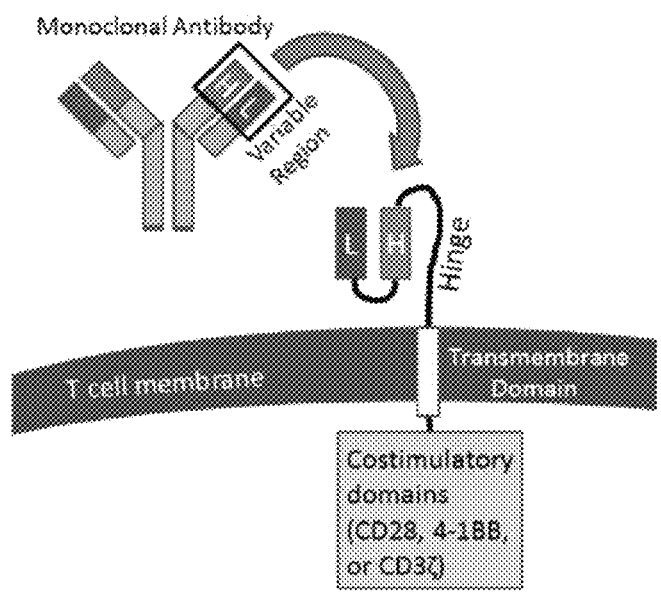
FIG. 4 shows a portion of a CARs transduced T-cell.

Reference is made to FIG. 4. A CARs transduced T-cells comprise single-chain variable fragments (scFv) from the variable region of a monoclonal antibody. In this example the monoclonal antibody is specific to human thymidine kinase 1 (TK1)

FIG. 5 is a schematic of a construct the signal peptide to which a chimeric antigen receptor will be added, which protein will be tranducted into the T-cells. It comprises an ectodomain signalling peptide based upon CB1 chains (k light chain attached to the scFv) and y heavy chain), a hinge portion based upon CDS, and an endodomain with costimulatory domains based upon CD28, CD3 zeta costimulatory protein receptors.

Figure 6:
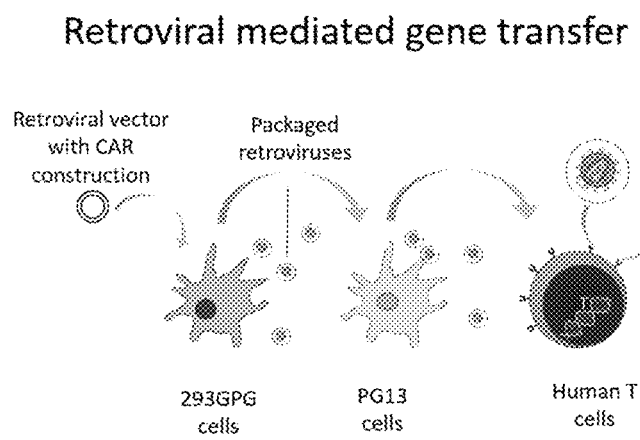
FIG. 6 shows a method for transduction illustrating the retroviral mediated gene transfer.

FIG. 6 illustrates a method for introducing any CAR protein by transduction into a T-cell and can be used in the present process. Chimeric antigen receptors (CARs) are genetically delivered fusion molecules that elicit T-cell activation upon binding of a native cell surface molecule. These molecules can be used to generate a large number of memory and effector T-cells that are capable of recognizing and attacking tumor cells. Most commonly, stable CAR expression is achieved in T-cells using retroviral vectors. In the method shown in FIG. 6, retroviral vectors are packaged in a two-step procedure. First, H29D human retroviral packaging cells (a derivative of 293 cells) are transfected with the vector of interest, which is packaged transiently in vesicular stomatitis virus (VSV) G pseudotyped particles. These particles are used to deliver the vector to PG13 cells, which achieve stable packaging of gibbon ape leukemia virus (GALV)-pseudotyped particles that are suitable for infection of human T-cells.

The key advantage of the method reported here is that it robustly generates polyclonal PG13 cells that are 100% positive for the vector of interest. This means that efficient gene transfer may be repeatedly achieved without the need to clone individual PG13 cells for experimental pre-clinical testing. To achieve T-cell transduction, cells must first be activated using a non-specific mitogen. Phytohemagglutinin (PHA) provides an economic and robust stimulus to achieve this. After 48-72 h, activated T-cells and virus-conditioned medium are mixed in RetroNectin-coated plasticware, which enhances transduction efficiency.

Transduced cells are analyzed for gene transfer efficiency by flow cytometry 48 h following transduction and may then be tested in several assays to evaluate CAR function, including target-dependent cytotoxicity, cytokine production and proliferation. (See Parente-Pereira A C, Wilkie S, van der Stegen S J C, Davies O M, Maher J. Use of retroviral-mediated gene transfer to deliver and test function of chimeric antigen receptors in human T-cells. J Biol Methods 2014; 1 (2):e7. doi: 10.14440/jbm.2014.30)

FIGS. 7A-7D illustrate the sequence of the DNA of the TK1 CART cell vector

FIG. 8 shows the protein sequence of the TK1 CART cell protein

FIG. 9 shows the TK1 CART cell Nucleotide and protein sequence alignment

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

REFERENCES

1. American Cancer Society, *Cancer Facts and Figures.* 2015.
2. Schreiber H. Tumor-specific immune responses. SeminImmunol 2008; 20:265-6; PMID:18977672; http://dx.doi.org/10.1016/j.smim.2008.10.001.
3. Stone, J. D. Aggen, D. H., Scheitinger, A, Schreiber, H, and Kranz, D. M. 2012 A sensitivity scale for targeting T cells with Chimeric Antigen Receptors (CARs) and Bispecific T-cell engagers (BiTEs) Onclommunology 1:6, 863-873
4. Schreiber H. Cancer Immunology. Philadelphia, Pa.: Lippincott-Williams & Wilkins 2012.
5. Karyampudi L, Knutson K L. Antibodies in cancer immunotherapy. Cancer Biomark 2010; 6:291-305; PMID:20938089.
6. Grillo-L.pez A J, White C A, Varns C, Shen D, Wei A, McClure A, et al. Overview of the clinical development of rituximab: first monoclonal antibody approved for the treatment of lymphoma. Semin Oneal 1999; 26:66-73; PMID: 10561020.
7. Goldenberg M M. Trastuzumab, a recombinant DNA derived humanized monoclonal antibody, a novel agent for the treatment of metastatic breast cancer. Clin Ther 1999; 21:309-18; PMID:10211534; http://dx.doi.org/10.1016/50149-2918(00)88288-0.
8. Seliger B, Cabrera T, Garrido F, Ferrone S. HLA class I antigen abnormalities and immune escape by malignant cells. Semin Cancer Biol 2002; 12:3-13; PMID: 11926409; http://dx.doi.org/10.1006/scbi.2001.0404.
9. Garrido F, Cabrera T, Concha A, Glew S, Ruiz-Cabello F, Stern P L. Natural history of HLA expression during tumour development. Immunol Today 1993; 14:491 9; PMID:8274189; http://dx.doi.org/10.1016/0167-5699 (93)90264-L.
10. Meidenbauer N, Zippelius A, Pittet M J, Laumer M, Vogl S, Heymann J, et al. High frequency of functionally active Melan-a-specific T cells in a patient with progressive immunoproteasome-deficient melanoma. Cancer Res 2004; 64:6319-26; PMID:15342421; http://dx.doi.org/10.1158/0008-5472.CAN-04-1341.
11. Yu Z, Theoret M R, Touloukian C E, Surman D R, Garman S C, Feigenbaum L, et al. Poor immunogenicity of a self/tumor antigen derives from peptide-MHCI instability and is independent of tolerance. J Clin Invest 2004; 114:551-9; PMID: 15314692.
12. Alegre. M, Robison, R. A. and O'Neill, K. L. Thymidine Kinase 1: A Universal Marker for Cancer. 2013 Cancer and Clinical Oncology 2013 vol 2: No 1; p 159-167.
13. O'Neill, K. L., Buckwalter, M. R., & Murray, B. K. (2001). Thymidine kinase: diagnostic and prognostic potential. Expert Rev Mal Diagn, 1 (4), 428-433. http://dx.doi.org/10.1586/14737159.1.4.428

What is claimed is:

1. A chimeric antigen receptor (CAR) comprising a targeting domain operatively linked to a signaling domain that polarizes a macrophage to an M1 macrophage
wherein the targeting domain and the signaling domain are heterogenous.

2. The CAR of claim 1, wherein the binding domain is a single-chain variable fragment (scFv).

3. The CAR of claim 2, wherein the scFv is specific for a human antigen.

4. The CAR of claim 1, wherein the signaling domain that polarizes a macrophage to an M1 macrophage is a human signaling domain that polarizes a macrophage to an M1 macrophage.

5. The CAR of claim 1, wherein the signaling domain that polarizes a macrophage to an M1 macrophage is a TLR4 domain.

6. A cell comprising the CAR of claim 1.

7. The cell of claim 6, wherein the cell is a monocyte or a macrophage.

8. The cell of claim 7, wherein the monocyte is a human monocyte or wherein the macrophage is a human macrophage.

* * * * *

SEQUENCE LISTING

<160> NUMBER OF SEQ ID NOS: 11

<210> SEQ ID NO 1
<211> LENGTH: 6967
<212> TYPE: DNA
<213> ORGANISM: Artificial Sequence
<220> FEATURE:
<223> OTHER INFORMATION: vector

<400> SEQUENCE: 1

```
tcaaggttag gaacagagag acaggagaat atgggccaaa caggatatct gtggtaagca      60
gttcctgccc cggctcaggg ccaagaacag ttggaacagc agaatatggg ccaaacagga     120
tatctgtggt aagcagttcc tgccccggct cagggccaag aacagatggt ccccagatgc     180
ggtcccgccc tcagcagttt ctagagaacc atcagatgtt tccagggtgc cccaaggacc     240
tgaaatgacc ctgtgcctta tttgaactaa ccaatcagtt cgcttctcgc ttctgttcgc     300
gcgcttctgc tccccgagct caataaaaga gcccacaacc cctcactcgg cgcgccagtc     360
ctccgattga ctgcgtcgcc cgggtacccg tattcccaat aaagcctctt gctgtttgca     420 tcggggggtct ttcatttgga ggttccaccg agatttggag accctgccc agggaccacc     480 gacccccccg ccgggaggta agctggccag cggtcgtttc gtgtctgtct ctgtctttgg     540
gcgtgtttgt gccggcatct aatgtttgcg cctgcgtctg tactagttgg ctaactagat     600
ctgtatctgg cggtcccgcg gaagaactga cgagttcgta ttcccggccg cagcccctgg     660
gagacgtccc agcggcctcg ggggcccgtt ttgtggccca ttctgtatca gttaacctac     720
ccgagtcgga cttttggag ctccgccact gtccgagggg tacgtggctt tgttggggga     780
cgagagacag agacacttcc cgcccccgtc tgaattttg ctttcggttt tacgccgaaa     840
ccgcgccgcg cgtcttgtct gctgcagcat cgttctgtgt tgtctctgtc tgactgtgtt     900
tctgtatttg tctgaaaatt agctcgacaa agttaagtaa tagtccctct ctccaagctc     960
acttacaggc ggccgcatgg attttcaagt gcagattatc agcttcctgc taatcagtgc    1020
ttcagtcata atgtccagag gacaaattgt tctctcccag tctccagcaa tcctgtctgc    1080
atctccaggg gagaaggtca caatgacttg cagggccagc tcaagtgtaa gttacatgca    1140
cttttaccaa cagaagccag gatcctcccc caaaccctga atttatgcca catccaacct    1200
ggcttctgga gtccctgctc gcttcagtgg cagtgggtct gggacctctt tctctctcac    1260
aatcagcaga gtggaggctg aagatgctgc cacttattac tgccagcagt ggagtagtaa    1320
cccacccacg ttcggctcgg ggacaaagtt ggaaataaaa tcaggtggag gagggtctgg    1380
```

```
tggtggtggt tctggcggag gaggctccat ggcagtggtt acaggggtca attcagaggt    1440
tcagctgcag cagtctgggg cagagcttgt gaagccaggg gcctcagtca agttgtcctg    1500
cacagcttct ggcttcaaca ttaaagacac ctatatacac tgggtgaagc agaggcctga    1560
acagggcctg gagtggattg gaaggattga tcctgcgaat ggtaatacta aatatgaccc    1620
gaagttccag ggcaaggcca ctataacaac agacacatcc ttcaacacag cctacctgca    1680
gctcagcagc ctgacatctg aggacactgc cgtctattac tgtgctaaag tgggttacgg    1740
ccactggtac ttcgatgtct ggggcgcagg gaccacggtc accgtctcct cagtcgacaa    1800
ggtgaacagc accacaacta aacctgtcct gagaactccc agtcctgtgc acccaactgg    1860
aacctcacag ccacagcgac cagaggattg ccgacctcgc gggagcgtga agggaaccgg    1920
actggacttc gcctgtgatt ctagtccaaa actcttttgg gcactggtgg tcgtggctgg    1980
cgtgctcttt tgctacggac tcctggtcac tgtggccctg tgcgtgatct ggaccaactc    2040
caggagaaat agactcctgc aggtgaccac aatgaacatg ccccctcggc gcccaggact    2100
gacacgcaag ccataccagc cttatgcccc agccaggac ttcgcagcat atagaccagc    2160
acacgcccgg gctaagttca gcaggagcgc cgagacagct gcaaacctcc aggatcctaa    2220
tcagctgtac aacgaactca atctggggcg aagggaggaa tatgacgtgc tggagaagaa    2280
acgagcaagg gatcccgaaa tgggcggaaa gcagcagaga cggcgcaacc ctcaggaggg    2340
agtgtacaat gctctgcaga aggacaaaat ggcagaggcc tattccgaaa ttgggaccaa    2400
gggtgaacga aggagaggga aaggtcatga tggcctgtac cagggactgt ccaccgctac    2460
caaggatacc tatgacgcac tccacatgca gaccctcgcc cccagatgag agaattcgag    2520
catcttaccg ccatttattc ccatatttgt tctgtttttc ttgatttggg tatacattta    2580
aatgttaata aaacaaaatg gtggggcaat catttacatt ttatgggata tgtaattact    2640
agttcaggtg tattgccaca agacaaacat gttaagaaac tttcccgtta tttacgctct    2700
gttcctgtta atcaacctct ggattacaaa atttgtgaaa gattgactga tattcttaac    2760
tatgttgctc cttttacgct gtgtggatat gctgctttaa tgcctctgta tcatgctatt    2820
gcttcccgta cggctttcgt tttctcctcc ttgtataaat cctggttgct gtctctttat    2880
gaggagttgt ggcccgttgt ccgtcaacgt ggcgtggtgt gctctgtgtt tgctgacgca    2940 accccactg gctggggcat tgccaccacc tgtcaactcc tttctgggac tttcgctttc    3000
cccctcccga tcgccacggc agaactcatc gccgcctgcc ttgcccgctg ctggacaggg    3060
gctaggttgc tgggcactga taattccgtg gtgttgtcgg ggaagctgac gtcctttcca    3120
tggctgctcg cctgtgttgc caactggatc ctgcgcggga cgtccttctg ctacgtccct    3180
tcggctctca atccagcgga cctcccttcc cgaggcttc tgccggttct gcggcctctc    3240
ccgcgtcttc gctttcggcc tccgacgagt cggatctccc tttgggccgc ctccccgcct    3300
gtttcgcctc ggcgtccggt ccgtgttgct tggtcgtcac ctgtgcagaa ttgcgaacca    3360
tggattccac cgtgaacttt gtctcctggc atgcaaatcg tcaacttggc atgccaagaa    3420
ttaattcgga tccaagctta ggcctgctcg ctttcttgct gtcccatttc tattaaaggt    3480
tcctttgttc cctaagtcca actactaaac tgggggatat tatgaagggc cttgagcatc    3540
tggattctgc ctagcgctaa gcttcctaac acgagccata gatagaataa agatttttat    3600
ttagtctcca gaaaaagggg ggaatgaaag accccacctg taggtttggc aagctagctt    3660
aagtaagcca ttttgcaagg catggaaaaa tacataactg agaatagaga agttcagatc    3720
aaggttagga acagagagac aggagaatat gggccaaaca ggatatctgt ggtaagcagt    3780
```

```
tcctgcccg gctcagggcc aagaacagtt ggaacagcag aatatgggcc aaacaggata    3840
tctgtggtaa gcagttcctg ccccggctca gggccaagaa cagatggtcc ccagatgcgg    3900
tcccgccctc agcagtttct agagaaccat cagatgtttc cagggtgccc caaggacctg    3960
aaatgaccct gtgccttatt tgaactaacc aatcagttcg cttctcgctt ctgttcgcgc    4020
gcttctgctc cccgagctca ataaaagagc ccacaacccc tcactcggcg cgccagtcct    4080
ccgatagact gcgtcgcccg ggtacccgt attcccaata agcctcttg ctgtttgcat     4140 ccgaatcgtg gactcgctga tccttgggag ggtctcctca gattgattga ctgcccacct    4200
cgggggtctt tcattctcga gagctttggc gtaatcatgg tcatagctgt ttcctgtgtg    4260
aaattgttat ccgctcacaa ttccacacaa catacgagcc ggaagcataa agtgtaaagc    4320
ctggggtgcc taatgagtga gctaactcac attaattgcg ttgcgctcac tgcccgcttt    4380
ccagtcggga aacctgtcgt gccagctgca ttaatgaatc ggccaacgcg cggggagagg    4440
cggtttgcgt attgggcgct cttccgcttc ctcgctcact gactcgctgc gctcggtcgt    4500
tcggctgcgg cgagcggtat cagctcactc aaaggcggta atacggttat ccacagaatc    4560
aggggataac gcaggaaaga acatgtgagc aaaaggccag caaaaggcca ggaaccgtaa    4620
aaaggccgcg ttgctggcgt ttttccatag gctccgcccc cctgacgagc atcacaaaaa    4680
tcgacgctca agtcagaggt ggcgaaaccc gacaggacta taaagatacc aggcgtttcc    4740
ccctggaagc tccctcgtgc gctctcctgt tccgaccctg ccgcttaccg gatacctgtc    4800
cgcctttctc ccttcgggaa gcgtggcgct ttctcaatgc tcacgctgta ggtatctcag    4860
ttcggtgtag gtcgttcgct ccaagctggg ctgtgtgcac gaaccccccg ttcagcccga    4920
ccgctgcgcc ttatccggta actatcgtct tgagtccaac ccggtaagac acgacttatc    4980
gccactggca gcagccactg gtaacaggat tagcagagcg aggtatgtag gcggtgctac    5040
agagttcttg aagtggtggc ctaactacgg ctacactaga aggacagtat ttggtatctg    5100
cgctctgctg aagccagtta ccttcggaaa aagagttggt agctcttgat ccggcaaaca    5160
aaccaccgct ggtagcggtg gtttttttgt ttgcaagcag cagattacgc gcagaaaaaa    5220
aggatctcaa gaagatcctt tgatctttc tacggggtct gacgctcagt ggaacgaaaa    5280
ctcacgttaa gggattttgg tcatgagatt atcaaaaagg atcttcacct agatcctttt    5340
aaattaaaaa tgaagtttta atcaatcta agtatatat gagtaaactt ggtctgacag     5400
ttaccaatgc ttaatcagtg aggcacctat ctcagcgatc tgtctatttc gttcatccat    5460
agttgcctga ctccccgtcg tgtagataac tacgatacgg gagggcttac catctggccc    5520
cagtgctgca atgataccgc gagacccacg ctcaccggct ccagatttat cagcaataaa    5580
ccagccagcc ggaagggccg agcgcagaag tggtcctgca actttatccg cctccatcca    5640
gtctattaat tgttgccggg aagctagagt aagtagttcg ccagttaata gtttgcgcaa    5700
cgttgttgcc attgctgctg gcatcgtggt gtcacgctcg tcgtttggta tggcttcatt    5760
cagctccggt tcccaacgat caaggcgagt tacatgatcc cccatgttgt gcaaaaaagc    5820
ggttagctcc ttcggtcctc cgatcgttgt cagaagtaag ttggccgcag tgttatcact    5880
catggttatg gcagcactgc ataattctct tactgtcatg ccatccgtaa gatgcttttc    5940
tgtgactggt gagtactcaa ccaagtcatt ctgagaatag tgtatgcggc gaccgagttg    6000
ctcttgcccg gcgtcaatac gggataatac cgcgccacat agcagaactt taaaagtgct    6060
catcattgga aaacgttctt cggggcgaaa actctcaagg atcttaccgc tgttgagatc    6120
```

```
cagttcgatg taacccactc gtgcacccaa ctgatcttca gcatctttta ctttcaccag    6180
cgtttctggg tgagcaaaaa caggaaggca aaatgccgca aaaaaggaa taagggcgac     6240 acggaaatgt tgaatactca tactcttcct ttttcaatat tattgaagca tttatcaggg    6300
ttattgtctc atgagcggat acatatttga atgtatttag aaaaataaac aaataggggt    6360
tccgcgcaca tttccccgaa aagtgccacc tgacgtctaa gaaaccatta ttatcatgac    6420
attaacctat aaaaataggc gtatcacgag gccctttcgt cttcaagctg cctcgcgcgt    6480
ttcggtgatg acggtgaaaa cctctgacac atgcagctcc cggagacggt cacagcttgt    6540
ctgtaagcgg atgccgggag cagacaagcc cgtcagggcg cgtcagcggg tgttggcggg    6600
tgtcggggcg cagccatgac ccagtcacgt agcgatagtt actatgcggc atcagagcag    6660
attgtactga gagtgcacca tatgcggtgt gaaataccgc acagatgcgt aaggagaaaa    6720
taccgcatca ggcgccattc gccattcagg ctgcgcaact gttgggaagg gcgatcggtg    6780
cgggcctctt cgctattacg ccagctggcg aaggggggat gtgctgcaag gcgattaagt    6840
tgggtaacgc cagggttttc ccagtcacga cgttgtaaaa cgacggccag tgaattagta    6900
ctctagctta agtaagccat tttgcaaggc atggaaaaat acataactga aatagagaa    6960 gttcaga                                                              6967
```

```
<210> SEQ ID NO 2
<211> LENGTH: 18
<212> TYPE: PRT
<213> ORGANISM: Artificial Sequence
<220> FEATURE:
<223> OTHER INFORMATION: vector

<400> SEQUENCE: 2

Met Asp Phe Gln Val Gln Ile Ile Ser Phe Leu Leu Ile Ser Ala Ser
1               5                   10                  15

Val Ile

<210> SEQ ID NO 3
<211> LENGTH: 110
<212> TYPE: PRT
<213> ORGANISM: Artificial Sequence
<220> FEATURE:
<223> OTHER INFORMATION: vector

<400> SEQUENCE: 3

Met Ser Arg Gly Gln Ile Val Leu Ser Gln Ser Pro Ala Ile Leu Ser
1               5                   10                  15

Ala Ser Pro Gly Glu Lys Val Thr Met Thr Cys Arg Ala Ser Ser Ser
                20                  25                  30

Val Ser Tyr Met His Phe Tyr Gln Gln Lys Pro Gly Ser Ser Pro Lys
            35                  40                  45

Pro Trp Ile Tyr Ala Thr Ser Asn Leu Ala Ser Gly Val Pro Ala Arg
        50                  55                  60

Phe Ser Gly Ser Gly Ser Gly Thr Ser Phe Ser Leu Thr Ile Ser Arg
65                  70                  75                  80

Val Glu Ala Glu Asp Ala Ala Thr Tyr Tyr Cys Gln Gln Trp Ser Ser
                85                  90                  95

Asn Pro Pro Thr Phe Gly Ser Gly Thr Lys Leu Glu Ile Lys
                100                 105                 110

<210> SEQ ID NO 4
<211> LENGTH: 16
```

```
<212> TYPE: PRT
<213> ORGANISM: Artificial Sequence
<220> FEATURE:
<223> OTHER INFORMATION: vector

<400> SEQUENCE: 4

Ser Gly Gly Gly Gly Ser Gly Gly Gly Ser Gly Gly Gly Ser
1               5                   10                  15

<210> SEQ ID NO 5
<211> LENGTH: 130
<212> TYPE: PRT
<213> ORGANISM: Artificial Sequence
<220> FEATURE:
<223> OTHER INFORMATION: vector

<400> SEQUENCE: 5

Met Ala Val Val Thr Gly Val Asn Ser Glu Val Gln Leu Gln Gln Ser
1               5                   10                  15

Gly Ala Glu Leu Val Lys Pro Gly Ala Ser Val Lys Leu Ser Cys Thr
            20                  25                  30

Ala Ser Gly Phe Asn Ile Lys Asp Thr Tyr Ile His Trp Val Lys Gln
        35                  40                  45

Arg Pro Glu Gln Gly Leu Glu Trp Ile Gly Arg Ile Asp Pro Ala Asn
    50                  55                  60

Gly Asn Thr Lys Tyr Asp Pro Lys Phe Gln Gly Lys Ala Thr Ile Thr
65                  70                  75                  80

Thr Asp Thr Ser Phe Asn Thr Ala Tyr Leu Gln Leu Ser Ser Leu Thr
                85                  90                  95

Ser Glu Asp Thr Ala Val Tyr Tyr Cys Ala Lys Val Gly Tyr Gly His
            100                 105                 110

Trp Tyr Phe Asp Val Trp Gly Ala Gly Thr Thr Val Thr Val Ser Ser
        115                 120                 125

Val Asp
    130

<210> SEQ ID NO 6
<211> LENGTH: 47
<212> TYPE: PRT
<213> ORGANISM: Artificial Sequence
<220> FEATURE:
<223> OTHER INFORMATION: vector

<400> SEQUENCE: 6

Lys Val Asn Ser Thr Thr Thr Lys Pro Val Leu Arg Thr Pro Ser Pro
1               5                   10                  15

Val His Pro Thr Gly Thr Ser Gln Pro Gln Arg Pro Glu Asp Cys Arg
            20                  25                  30

Pro Arg Gly Ser Val Lys Gly Thr Gly Leu Asp Phe Ala Cys Asp
        35                  40                  45

<210> SEQ ID NO 7
<211> LENGTH: 76
<212> TYPE: PRT
<213> ORGANISM: Artificial Sequence
<220> FEATURE:
<223> OTHER INFORMATION: vector

<400> SEQUENCE: 7

Ser Ser Pro Lys Leu Phe Trp Ala Leu Val Val Val Ala Gly Val Leu
1               5                   10                  15
```

```
Phe Cys Tyr Gly Leu Leu Val Thr Val Ala Leu Cys Val Ile Trp Thr
                20                  25                  30

Asn Ser Arg Arg Asn Arg Leu Leu Gln Val Thr Thr Met Asn Met Thr
            35                  40                  45

Pro Arg Arg Pro Gly Leu Thr Arg Lys Pro Tyr Gln Pro Tyr Ala Pro
        50                  55                  60

Ala Arg Asp Phe Ala Ala Tyr Arg Pro Ala His Ala
65                  70                  75
```

<210> SEQ ID NO 8
<211> LENGTH: 113
<212> TYPE: PRT
<213> ORGANISM: Artificial Sequence
<220> FEATURE:
<223> OTHER INFORMATION: vector

<400> SEQUENCE: 8

```
Arg Ala Lys Phe Ser Arg Ser Ala Glu Thr Ala Ala Asn Leu Gln Asp
1               5                   10                  15

Pro Asn Gln Leu Tyr Asn Glu Leu Asn Leu Gly Arg Arg Glu Glu Tyr
                20                  25                  30

Asp Val Leu Glu Lys Lys Arg Ala Arg Asp Pro Glu Met Gly Gly Lys
            35                  40                  45

Gln Gln Arg Arg Arg Asn Pro Gln Glu Gly Val Tyr Asn Ala Leu Gln
        50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Thr Leu Ala Pro
            100                 105                 110

Arg
```

<210> SEQ ID NO 9
<211> LENGTH: 1533
<212> TYPE: DNA
<213> ORGANISM: Artificial Sequence
<220> FEATURE:
<223> OTHER INFORMATION: vector

<400> SEQUENCE: 9

```
atggattttc aagtgcagat tatcagcttc ctgctaatca gtgcttcagt cataatgtcc      60
agaggacaaa ttgttctctc ccagtctcca gcaatcctgt ctgcatctcc aggggagaag     120
gtcacaatga cttgcagggc cagctcaagt gtaagttaca tgcactttta ccaacagaag     180
ccaggatcct cccccaaacc ctggatttat gccacatcca acctggcttc tggagtccct     240
gctcgcttca gtggcagtgg gtctgggacc tctttctctc tcacaatcag cagagtggag     300
gctgaagatg ctgccactta ttactgccag cagtggagta gtaacccacc cacgttcggc     360
tcggggacaa agttggaaat aaaatcaggt ggaggagggt ctggtggtgg tggttctggc     420
ggaggaggct ccatggcagt ggttacaggg gtcaattcag aggttcagct gcagcagtct     480
ggggcagagc ttgtgaagcc aggggcctca gtcaagttgt cctgcacagc ttctggcttc     540
aacattaaag acacctatat acactgggtg aagcagaggc tgaacagggc ctggagtgg      600 attggaagga ttgatcctgc gaatggtaat actaaatatg acccgaagtt ccagggcaag     660
gccactataa caacagacac atccttcaac acagcctacc tgcagctcag cagcctgaca     720
```

| | |
|---|---|
| tctgaggaca ctgccgtcta ttactgtgct aaagtgggtt acggccactg gtacttcgat | 780 |
| gtctggggcg cagggaccac ggtcaccgtc tcctcagtcg acaaggtgaa cagcaccaca | 840 |
| actaaacctg tcctgagaac tcccagtcct gtgcacccaa ctggaacctc acagccacag | 900 |
| cgaccagagg attgccgacc tcgcgggagc gtgaagggaa ccggactgga cttcgcctgt | 960 |
| gattctagtc caaaactctt tgggcactg gtggtcgtgg ctggcgtgct cttttgctac | 1020 |
| ggactcctgg tcactgtggc cctgtgcgtg atctggacca actccaggag aaatagactc | 1080 |
| ctgcaggtga ccacaatgaa catgaccct cggcgcccag gactgacacg caagccatac | 1140 |
| cagccttatg ccccagccag ggacttcgca gcatatagac cagcacacgc ccgggctaag | 1200 |
| ttcagcagga gcgccgagac agctgcaaac ctccaggatc ctaatcagct gtacaacgaa | 1260 |
| ctcaatctgg ggcgaaggga ggaatatgac gtgctggaga agaaacgagc aagggatccc | 1320 |
| gaaatgggcg gaaagcagca gagacggcgc aaccctcagg agggagtgta caatgctctg | 1380 |
| cagaaggaca aaatggcaga ggcctattcc gaaattggga ccaagggtga acgaaggaga | 1440 |
| gggaaaggtc atgatggcct gtaccaggga ctgtccaccg ctaccaagga tacctatgac | 1500 |
| gcactccaca tgcagaccct cgcccccaga tga | 1533 |

<210> SEQ ID NO 10
<211> LENGTH: 6967
<212> TYPE: DNA
<213> ORGANISM: Artificial Sequence
<220> FEATURE:
<223> OTHER INFORMATION: vector

<400> SEQUENCE: 10

| | |
|---|---|
| tcaaggttag gaacagagag acaggagaat atgggccaaa caggatatct gtggtaagca | 60 |
| gttcctgccc cggctcaggg ccaagaacag ttggaacagc agaatatggg ccaaacagga | 120 |
| tatctgtggt aagcagttcc tgccccggct cagggccaag aacagatggt ccccagatgc | 180 |
| ggtcccgccc tcagcagttt ctagagaacc atcagatgtt tccagggtgc cccaaggacc | 240 |
| tgaaatgacc ctgtgcctta tttgaactaa ccaatcagtt cgcttctcgc ttctgttcgc | 300 |
| gcgcttctgc tccccgagct caataaaaga gcccacaacc cctcactcgg cgcgccagtc | 360 |
| ctccgattga ctgcgtcgcc cgggtacccg tattcccaat aaagcctctt gctgtttgca | 420 |
| tcggggtct ttcatttgga ggttccaccg agatttggag accccctgccc agggaccacc | 480 |
| gacccccccg ccgggaggta agctggccag cggtcgtttc gtgtctgtct ctgtctttgg | 540 |
| gcgtgttttgt gccggcatct aatgtttgcg cctgcgtctg tactagttgg ctaactagat | 600 |
| ctgtatctgg cggtcccgcg gaagaactga cgagttcgta ttcccggccg cagcccctgg | 660 |
| gagacgtccc agcggcctcg ggggcccgtt ttgtggccca ttctgtatca gttaacctac | 720 |
| ccgagtcgga cttttttggag ctccgccact gtccgagggg tacgtggctt tgttggggga | 780 |
| cgagagacag agacacttcc cgcccccgtc tgaattttttg ctttcggttt tacgccgaaa | 840 |
| ccgcgccgcg cgtcttgtct gctgcagcat cgttctgtgt tgtctctgtc tgactgtgtt | 900 |
| tctgtatttg tctgaaaatt agctcgacaa agttaagtaa tagtccctct ctccaagctc | 960 |
| acttacaggc ggccgcatgg attttcaagt gcagattatc agcttcctgc taatcagtgc | 1020 |
| ttcagtcata atgtccagag acaaattgt tctctcccag tctccagcaa tcctgtctgc | 1080 |
| atctccaggg gagaaggtca caatgacttg cagggccagc tcaagtgtaa gttacatgca | 1140 |
| ctttaccaa cagaagccag gatcctcccc caaaccctgg atttatgcca catccaacct | 1200 |
| ggcttctgga gtccctgctc gcttcagtgg cagtgggtct gggacctctt tctctctcac | 1260 |

```
aatcagcaga gtggaggctg aagatgctgc acttattac tgccagcagt ggagtagtaa    1320
cccacccacg ttcggctcgg ggacaaagtt ggaaataaaa tcaggtggag gagggtctgg    1380
tggtggtggt tctggcgag gaggctccat ggcagtggtt acaggggtca attcagaggt    1440
tcagctgcag cagtctgggg cagagcttgt gaagccaggg gcctcagtca agttgtcctg    1500
cacagcttct ggcttcaaca ttaaagacac ctatatacac tgggtgaagc agaggcctga    1560
acagggcctg gagtggattg aaggattga tcctgcgaat ggtaatacta aatatgaccc    1620
gaagttccag ggcaaggcca ctataacaac agacacatcc ttcaacacag cctacctgca    1680
gctcagcagc ctgacatctg aggacactgc cgtctattac tgtgctaaag tgggttacgg    1740
ccactggtac ttcgatgtct ggggcgcagg gaccacggtc accgtctcct cagtcgacaa    1800
ggtgaacagc accacaacta aacctgtcct gagaactccc agtcctgtgc acccaactgg    1860
aacctcacag ccacagcgac cagaggattg ccgacctcgc gggagcgtga agggaaccgg    1920
actggacttc gcctgtgatt ctagtccaaa actcttttgg gcactggtgg tcgtggctgg    1980
cgtgctcttt tgctacggac tcctggtcac tgtggccctg tgcgtgatct ggaccaactc    2040
caggagaaat agactcctgc aggtgaccac aatgaacatg acccctcggc gcccaggact    2100
gacacgcaag ccataccagc cttatgcccc agccagggac ttcgcagcat atagaccagc    2160
acacgcccgg gctaagttca gcaggagcgc cgagacagct gcaaacctcc aggatcctaa    2220
tcagctgtac aacgaactca atctggggcg aagggaggaa tatgacgtgc tggagaagaa    2280
acgagcaagg gatcccgaaa tgggcggaaa gcagcagaga cggcgcaacc ctcaggaggg    2340
agtgtacaat gctctgcaga aggacaaaat ggcagaggcc tattccgaaa ttgggaccaa    2400
gggtgaacga aggagaggga aaggtcatga tggcctgtac cagggactgt ccaccgctac    2460
caaggatacc tatgacgcac tccacatgca gacccctcgcc cccagatgag agaattcgag    2520
catcttaccg ccatttattc ccatatttgt tctgtttttc ttgatttggg tatacattta    2580
aatgttaata aaacaaaatg gtggggcaat catttacatt ttatgggata tgtaattact    2640
agttcaggtg tattgccaca agacaaacat gttaagaaac tttcccgtta tttacgctct    2700
gttcctgtta atcaacctct ggattacaaa atttgtgaaa gattgactga tattcttaac    2760
tatgttgctc cttttacgct gtgtggatat gctgctttaa tgcctctgta tcatgctatt    2820
gcttcccgta cggctttcgt tttctcctcc ttgtataaat cctggttgct gtctctttat    2880
gaggagttgt ggcccgttgt ccgtcaacgt ggcgtggtgt gctctgtgtt gctgacgca     2940 accccccactg gctggggcat tgccaccacc tgtcaactcc tttctgggac tttcgctttc    3000 ccctcccga tcgccacggc agaactcatc gccgcctgcc ttgcccgctg ctggacaggg    3060
gctaggttgc tgggcactga taattccgtg gtgttgtcgg ggaagctgac gtcctttcca    3120
tggctgctcg cctgtgttgc caactggatc ctgcgcggga cgtccttctg ctacgtccct    3180
tcggctctca atccagcgga cctcccttcc cgaggcttc tgccggttct gcggcctctc    3240
ccgcgtcttc gctttcggcc tccgacgagt cggatctccc tttgggccgc ctccccgcct    3300
gtttcgcctc ggcgtccggt ccgtgttgct tggtcgtcac ctgtgcagaa ttgcgaacca    3360
tggattccac cgtgaacttt gtctcctggc atgcaaatcg tcaacttggc atgccaagaa    3420
ttaattcgga tccaagctta ggcctgctcg ctttcttgct gtcccatttc tattaaaggt    3480 tccttttgttc cctaagtcca actactaaac tgggggatat tatgaagggc cttgagcatc    3540
tggattctgc ctagcgctaa gcttcctaac acgagccata gatagaataa aagattttat    3600
```

-continued

```
ttagtctcca gaaaaagggg ggaatgaaag accccacctg taggtttggc aagctagctt      3660
aagtaagcca ttttgcaagg catggaaaaa tacataactg agaatagaga agttcagatc      3720
aaggttagga acagagagac aggagaatat gggccaaaca ggatatctgt ggtaagcagt      3780
tcctgccccg gctcagggcc aagaacagtt ggaacagcag aatatgggcc aaacaggata      3840
tctgtggtaa gcagttcctg ccccggctca gggccaagaa cagatggtcc ccagatgcgg      3900
tcccgccctc agcagtttct agagaaccat cagatgtttc cagggtgccc aaggacctg       3960 aaatgaccct gtgccttatt tgaactaacc aatcagttcg cttctcgctt ctgttcgcgc      4020
gcttctgctc cccgagctca ataaaagagc ccacaacccc tcactcggcg cgccagtcct      4080
ccgatagact gcgtcgcccg ggtacccgt attcccaata aagcctcttg ctgtttgcat       4140
ccgaatcgtg gactcgctga tccttgggag ggtctcctca gattgattga ctgcccacct      4200
cgggggtctt tcattctcga gagctttggc gtaatcatgg tcatagctgt ttcctgtgtg     4260
aaattgttat ccgctcacaa ttccacacaa catacgagcc ggaagcataa agtgtaaagc      4320
ctggggtgcc taatgagtga gctaactcac attaattgcg ttgcgctcac tgcccgcttt     4380
ccagtcggga acctgtcgt gccagctgca ttaatgaatc ggccaacgcg cggggagagg       4440
cggtttgcgt attgggcgct cttccgcttc ctcgctcact gactcgctgc gctcggtcgt      4500
tcggctgcgg cgagcggtat cagctcactc aaaggcggta atacggttat ccacagaatc     4560
aggggataac gcaggaaaga acatgtgagc aaaaggccag caaaaggcca ggaaccgtaa      4620
aaaggccgcg ttgctggcgt ttttccatag gctccgcccc cctgacgagc atcacaaaaa      4680
tcgacgctca agtcagaggt ggcgaaaccc gacaggacta taaagatacc aggcgtttcc      4740
ccctggaagc tccctcgtgc gctctcctgt tccgaccctg ccgcttaccg gatacctgtc      4800
cgcctttctc ccttcgggaa gcgtggcgct ttctcaatgc tcacgctgta ggtatctcag      4860
ttcggtgtag gtcgttcgct ccaagctggg ctgtgtgcac gaaccccccg ttcagcccga      4920
ccgctgcgcc ttatccggta actatcgtct gagtccaac ccggtaagac acgacttatc       4980
gccactggca gcagccactg gtaacaggat tagcagagcg aggtatgtag gcggtgctac      5040
agagttcttg aagtggtggc ctaactacgg ctacactaga aggacagtat ttggtatctg      5100
cgctctgctg aagccagtta ccttcggaaa aagagttggt agctcttgat ccggcaaaca      5160
aaccaccgct ggtagcggtg gtttttttgt ttgcaagcag cagattacgc gcagaaaaaa      5220
aggatctcaa gaagatcctt tgatctttc tacggggtct gacgctcagt ggaacgaaaa       5280
ctcacgttaa gggattttgg tcatgagatt atcaaaaagg atcttcacct agatcctttt      5340
aaattaaaaa tgaagtttta aatcaatcta agtatatat gagtaaactt ggtctgacag       5400
ttaccaatgc ttaatcagtg aggcaccta t ctcagcgatc tgtctatttc gttcatccat     5460
agttgcctga ctccccgtcg tgtagataac tacgatacgg gagggcttac catctggccc      5520
cagtgctgca atgataccgc gagacccacg ctcaccggct ccagatttat cagcaataaa      5580
ccagccagcc ggaagggccg agcgcagaag tggtcctgca actttatccg cctccatcca      5640
gtctattaat tgttgccggg aagctagagt aagtagttcg ccagttaata gtttgcgcaa      5700
cgttgttgcc attgctgctg gcatcgtggt gtcacgctcg tcgtttggta tggcttcatt      5760
cagctccggt tcccaacgat caaggcgagt tacatgatcc cccatgttgt gcaaaaaagc      5820
ggttagctcc ttcggtcctc cgatcgttgt cagaagtaag ttggccgcag tgttatcact      5880
catggttatg gcagcactgc ataattctct tactgtcatg ccatccgtaa gatgcttttc      5940
tgtgactggt gagtactcaa ccaagtcatt ctgagaatag tgtatgcggc gaccgagttg      6000
```

```
ctcttgcccg gcgtcaatac gggataatac cgcgccacat agcagaactt taaaagtgct    6060
catcattgga aaacgttctt cggggcgaaa actctcaagg atcttaccgc tgttgagatc    6120
cagttcgatg taacccactc gtgcacccaa ctgatcttca gcatctttta ctttcaccag    6180
cgtttctggg tgagcaaaaa caggaaggca aaatgccgca aaaaagggaa taagggcgac    6240
acggaaatgt tgaatactca tactcttcct ttttcaatat tattgaagca tttatcaggg    6300
ttattgtctc atgagcggat acatatttga atgtatttag aaaaataaac aaatagggggt   6360 tccgcgcaca tttccccgaa aagtgccacc tgacgtctaa gaaaccatta ttatcatgac    6420
attaacctat aaaaataggc gtatcacgag gccctttcgt cttcaagctg cctcgcgcgt    6480
ttcggtgatg acggtgaaaa cctctgacac atgcagctcc cggagacggt cacagcttgt    6540
ctgtaagcgg atgccgggag cagacaagcc cgtcagggcg cgtcagcggg tgttggcggg    6600
tgtcggggcg cagccatgac ccagtcacgt agcgatagtt actatgcggc atcagagcag    6660
attgtactga gagtgcacca tatgcggtgt gaaataccgc acagatgcgt aaggagaaaa    6720
taccgcatca ggcgccattc gccattcagg ctgcgcaact gttgggaagg gcgatcggtg    6780
cgggcctctt cgctattacg ccagctggcg aaagggggat gtgctgcaag gcgattaagt    6840
tgggtaacgc cagggttttc ccagtcacga cgttgtaaaa cgacggccag tgaattagta    6900
ctctagctta agtaagccat tttgcaaggc atggaaaaat acataactga gaatagagaa    6960
gttcaga                                                              6967

<210> SEQ ID NO 11

<400> SEQUENCE: 11

000
```